United States Patent
Greyson et al.

(10) Patent No.: US 7,862,811 B2
(45) Date of Patent: Jan. 4, 2011

(54) PROTEASE INHIBITION FOR PREVENTION OR TREATMENT OF HEART FAILURE

(75) Inventors: Clifford Greyson, Greenwood Village, CO (US); Gregory Schwartz, Denver, CO (US)

(73) Assignee: Regents of the University of Colorado, Boulder, CO (US)

(*) Notice: Subject to any disclaimer, the term of this patent is extended or adjusted under 35 U.S.C. 154(b) by 1263 days.

(21) Appl. No.: 11/066,839

(22) Filed: Feb. 25, 2005

(65) Prior Publication Data

US 2005/0238633 A1   Oct. 27, 2005

Related U.S. Application Data

(60) Provisional application No. 60/548,801, filed on Feb. 27, 2004.

(51) Int. Cl.
*A61K 38/43* (2006.01)
(52) U.S. Cl. .......................................... 424/94.1
(58) Field of Classification Search .................. 424/94.1
See application file for complete search history.

(56) References Cited

U.S. PATENT DOCUMENTS

| | | | |
|---|---|---|---|
| 5,206,347 A | 4/1993 | Ruoslahti et al. |
| 5,223,409 A | 6/1993 | Ladner et al. |
| 5,622,699 A | 4/1997 | Ruoslahti et al. |
| 6,068,829 A | 5/2000 | Ruoslahti et al. |
| 6,102,926 A | 8/2000 | Tartaglia et al. |
| 6,120,520 A | 9/2000 | Saadat et al. |
| 6,251,104 B1 | 6/2001 | Kesten et al. |
| 6,309,370 B1 | 10/2001 | Haim et al. |
| 6,432,119 B1 | 8/2002 | Saadat |
| 6,485,481 B1 | 11/2002 | Pfeiffer |

OTHER PUBLICATIONS

Urthaler et al. MDL-28170, a membrane-permeant calpain inhibitor, attenuates stunning and PKC proteolysis in reperfused ferret hearts. Cardiovasc. Res. 1997; 35: 60-67.*
King et al. Use of nitric oxide for decompensated right ventricular failure and circulatory shock after cardiac arrest. Br. J. Anaesth. 2000; 85: 628-631.*
Tsuji et al. (Am. J. Physiol. Hear Circ. Physiol. 2001; 281: H1286-H1294).*
Greyson et al. (Cardiovasc. Res. 1997; 34: 281-288).*
Jordan, V. C. Nature Reviews: Drug Discovery, 2, 2003, pp. 205-213.*
Desai et al. (J. Med. Chem. 2004, 47, 6609-6615).*
Michael Heylin, C&EN News, Jul. 24, 2006; p. 43-52.*
Mani et al. (Am. J. Physiol. Heart Circ. Physiol., 295: H314-H326 (2008).*

* cited by examiner

*Primary Examiner*—Kamal A Saeed
*Assistant Examiner*—Valerie Rodriguez-Garcia
(74) *Attorney, Agent, or Firm*—Fulbright & Jaworski

(57) ABSTRACT

Methods, and compositions to prevent and/or treat acute or chronic right ventricular failure from pressure over load (RVPO). In one embodiment, the method includes the inhibition of at least one cysteine protease. In other embodiments, the method includes the inhibition of MMP activity to prevent or treat right ventricular failure from acute pressure over load (RVPO). In another embodiment, combination therapies are included to inhibit cysteine protease activity and MMP activity.

4 Claims, 12 Drawing Sheets

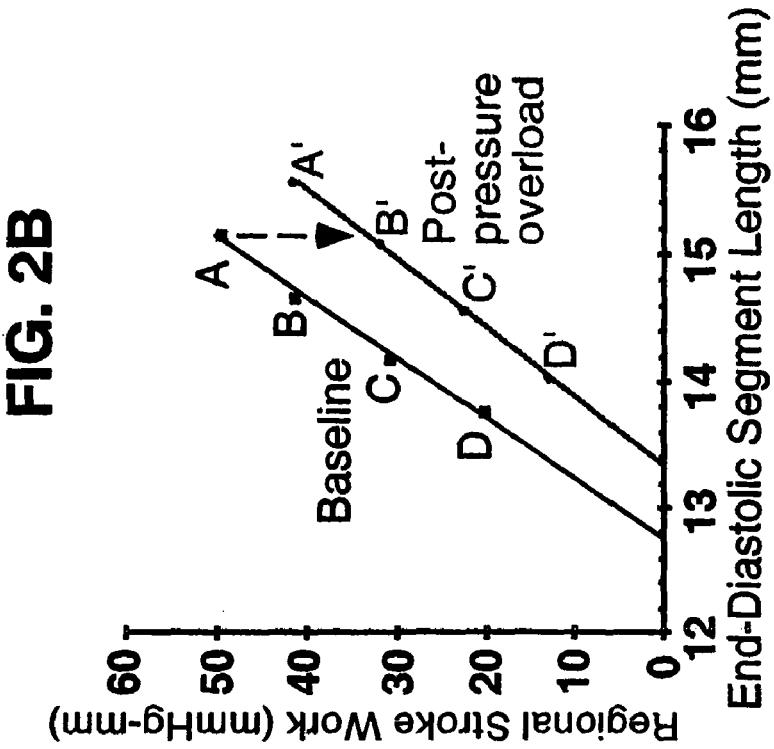
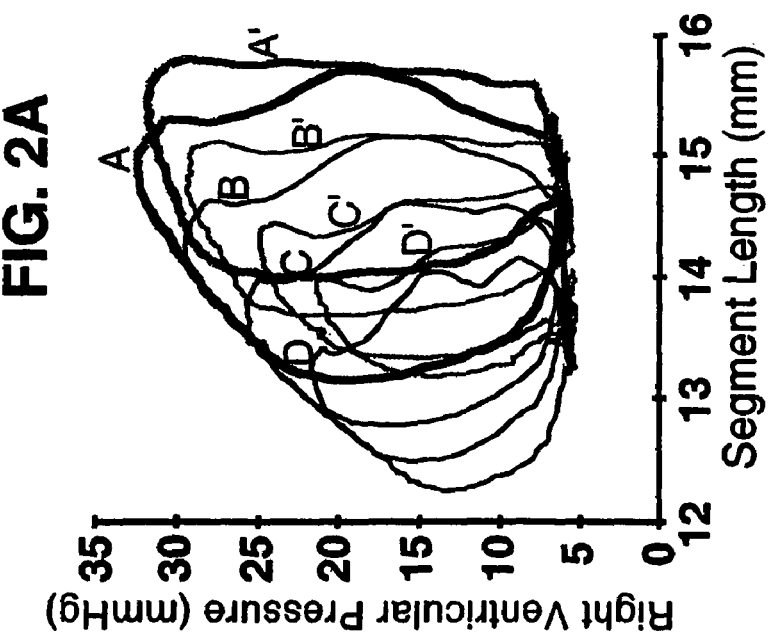
FIG. 2A
FIG. 2B

PROTEASE INHIBITION FOR PREVENTION OR TREATMENT OF HEART FAILURE

The present application claims the benefit under 35 U.S.C. §119(e) of provisional U.S. patent application Ser. No. 60/548,801, filed on Feb. 27, 2004. The present invention was supported a National Heart, Lung and Blood Institute R01 grant HL68606.

FIELD

The present invention relates generally to treatment of contractile failure of the heart. More particularly, the present invention relates to the treatment of right ventricular (RV) contractile failure. In addition, this invention also relates to materials, methods and treatments for the attenuation of right ventricular (RV) contractile failure from acute RV pressure overload by inhibition of proteases.

BACKGROUND

Right ventricular (RV) contractile failure from acute RV pressure overload is an important cause of morbidity and mortality in conditions such as massive pulmonary embolism, hypoxic pulmonary vasoconstriction, and following cardiopulmonary bypass and cardiac transplantation.(1) RV failure is a leading cause of early mortality in patients undergoing cardiac transplantation, and often requires inotropic support or ventricular assist devices.

RV stroke volume is depressed during acute RV pressure overload, it had been assumed that this was a direct and reversible consequence of the increase in afterload, and did not reflect alteration in intrinsic RV contractile function. Thus, standard therapeutic strategies for management of RV contractile failure have concentrated almost exclusively on maneuvers to reduce RV afterload, such as pulmonary thromboendarterectomy in pulmonary embolism or use of inhaled nitric oxide following cardiopulmonary bypass or cardiac transplant.(2, 3) While there is no question that global RV ejection fraction improves with such therapeutic maneuvers, mortality in these conditions remains high. Whether the persistently high mortality in these conditions results entirely from incomplete treatment of the underlying condition, or is due in part to intrinsic dysfunction of the RV, has not been possible to determine because it is not generally possible to determine whether intrinsic RV function normalizes in clinical studies: typically there is no baseline assessment of RV function prior to development of acute pulmonary hypertension, and ordinary clinical indices of RV function, determined by echocardiography or nuclear scans, are not loading condition independent. Measurement of loading condition-independent indices of regional contractile function in humans is technically difficult, and may be impossible in critically ill patients. Thus, the question of whether acute RV pressure overload results in intrinsic RV contractile function has remained unresolved.

Clinical recovery from acute RV pressure overload is strongly influenced by success in alleviating whatever condition is responsible for pressure overload in the first place; but it is the RV contractile dysfunction, rather than the pressure overload per se, that directly contributes to morbidity and mortality. Thus, any factors that affect the development of or recovery from RV contractile dysfunction may necessarily play direct and important roles in ultimate clinical outcome. To date, there has been little investigative activity directed toward the mechanism of RV contractile dysfunction in this setting and thus there has been little investigation of potential therapeutic interventions to directly attenuate the development of RV contractile dysfunction from acute pressure overload.

Recently, studies have demonstrated that intrinsic RV contractile function remains significantly depressed following even a brief period of pressure overload, despite complete restoration of normal loading conditions. The severity of RV dysfunction following pressure overload is directly related to the level of RV free wall stress during pressure overload.(4) Such contractile dysfunction, while qualitatively similar to myocardial dysfunction of the left ventricle (LV) following ischemia-reperfusion, appears not to be due to ischemia of the RV.(5)

Thus, there is a current need for intervention in subjects with RV pressure overload directed toward restoration of RV contractile function.

DESCRIPTIVE EMBODIMENTS

The following drawings form part of the present specification and are included to further demonstrate certain aspects of the present invention. The invention may be better understood by reference to one or more of these drawings in combination with the detailed description of specific embodiments presented herein.

FIG. 1. Illustrates an exemplary method of attenuation of RV contractile dysfunction and calpain activation after acute RV pressure overload by intracoronary administration of a protease inhibitor such as calpain inhibitor III (carbobenzoxy-valinyl-phenylalaninal) known as MDL-28170.

FIG. 2A illustrates regional pressure versus segment length relations in the RV free wall of a pig under baseline conditions (black lines) and one hour after restoration of baseline loading conditions (gray lines) following an hour of pressure overload. Bold loops A (baseline) and A' (post-pressure overload) were obtained under steady-state conditions before inferior vena cava occlusion. FIG. 2B shows regional Frank-Starling relations derived from the data in FIG. 2A. The use of the regional Frank-Starling relation to assess regional contractility is described in detail in the Example section. The rightward and downward shift in the regional Frank-Starling relation from baseline (black line) to one hour after restoration of baseline loading conditions (gray line) demonstrates persistent RV contractile dysfunction resulting from acute RV pressure overload. (see Example section)

FIG. 3 illustrates the correlation of recovery of RV preload-adjusted regional external work (a loading-condition independent index of regional contractile function) after acute RV pressure overload with the dysfunction predictor index, a surrogate for regional RV free wall stress. The four symbols indicate the experimental treatment groups: open circle: open pericardium, no dobutamine; open square: open pericardium, +dobutamine; closed circle: closed pericardium, no dobutamine; closed square: closed pericardium, dobutamine.

Figure 6:
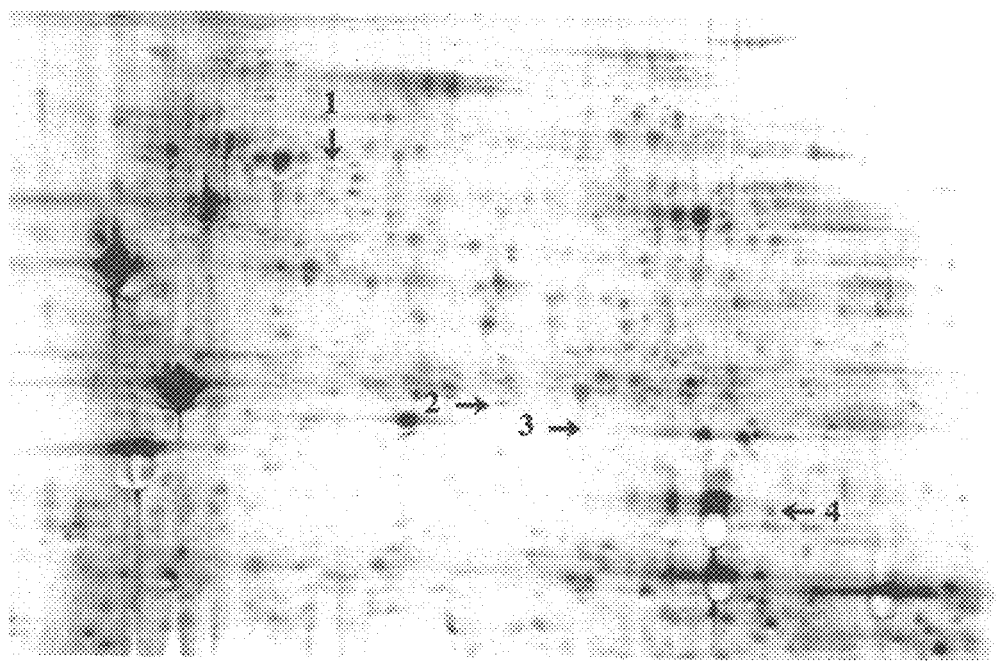

FIG. 6: illustrates an exemplary fluorescent two-dimensional difference gel electrophoresis image. RV pressure overload myocardium is stained with Cy3 and sham myocardium is stained with Cy5. Arrow numbers 2 and 4 indicate increased protein levels, while arrow numbers 1 and 3 indicate decreased protein levels.

Figure 7A:
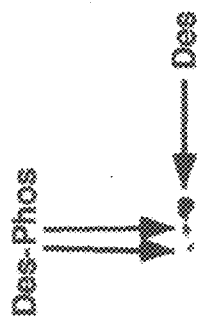
Figure 7B:
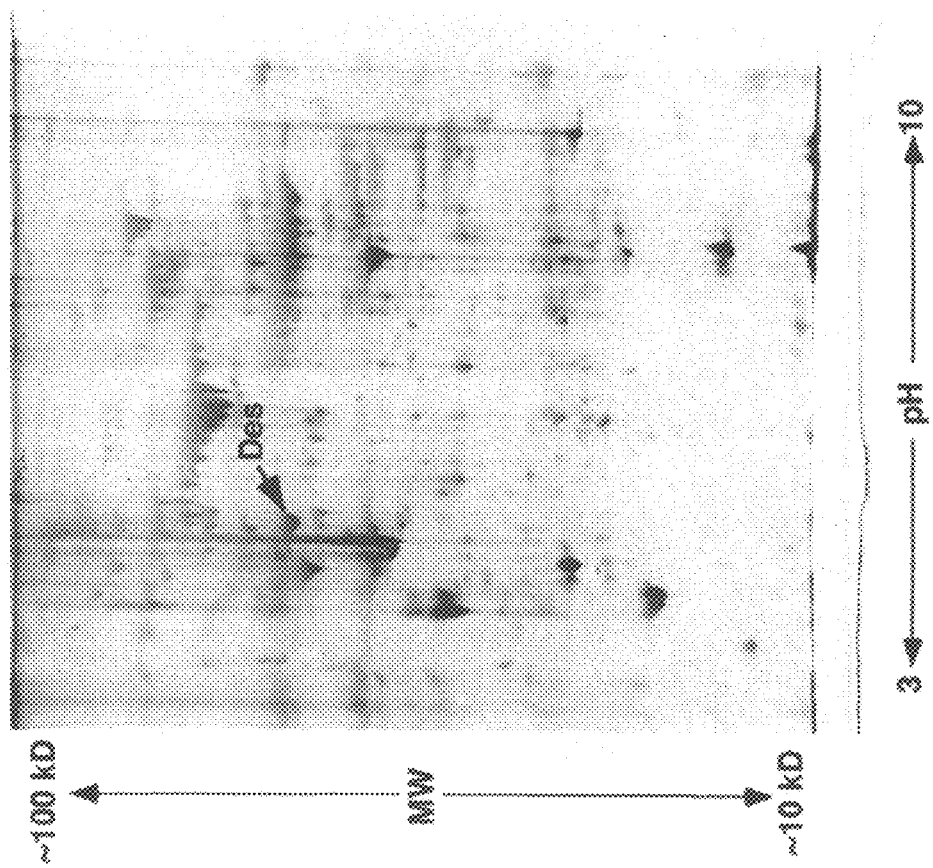

FIGS. 7A, and 7B represents an example of a Coomassie-stained 2-D PAGE gel of right ventricular myocardium (FIG. 7A) and its corresponding Western blot (obtained by direct transfer to a PVDF membrane) probed with polyclonal anti-desmin antibody (FIG. 7B) from a control pig. The spot marked Des in FIG. 7A was identified as pig desmin by MALDI-TOF mass spectrometry. The spots marked Des-Phos in the FIG. 7B are likely phosphorylated forms of desmin.

FIGS. 8A and 8B represents an example of a Coomassie-stained 2-D PAGE gel of right ventricular myocardium (FIG. 8A) and its corresponding Western blot probed with polyclonal anti-desmin antibody (FIG. 8B) from a pig subjected to 15 min acute right ventricular pressure overload. The spots marked Des-Phos have increased in abundance compared with the spots marked Des-Phos in the control pig (FIG. 7B), suggesting a shift from non-phosphorylated to phosphorylated desmin. The spots marked Des-Deg likely represent desmin degradation products. The identities of 40 to 50 kDa proteins spots marked Unk are not yet determined.

Figure 8:
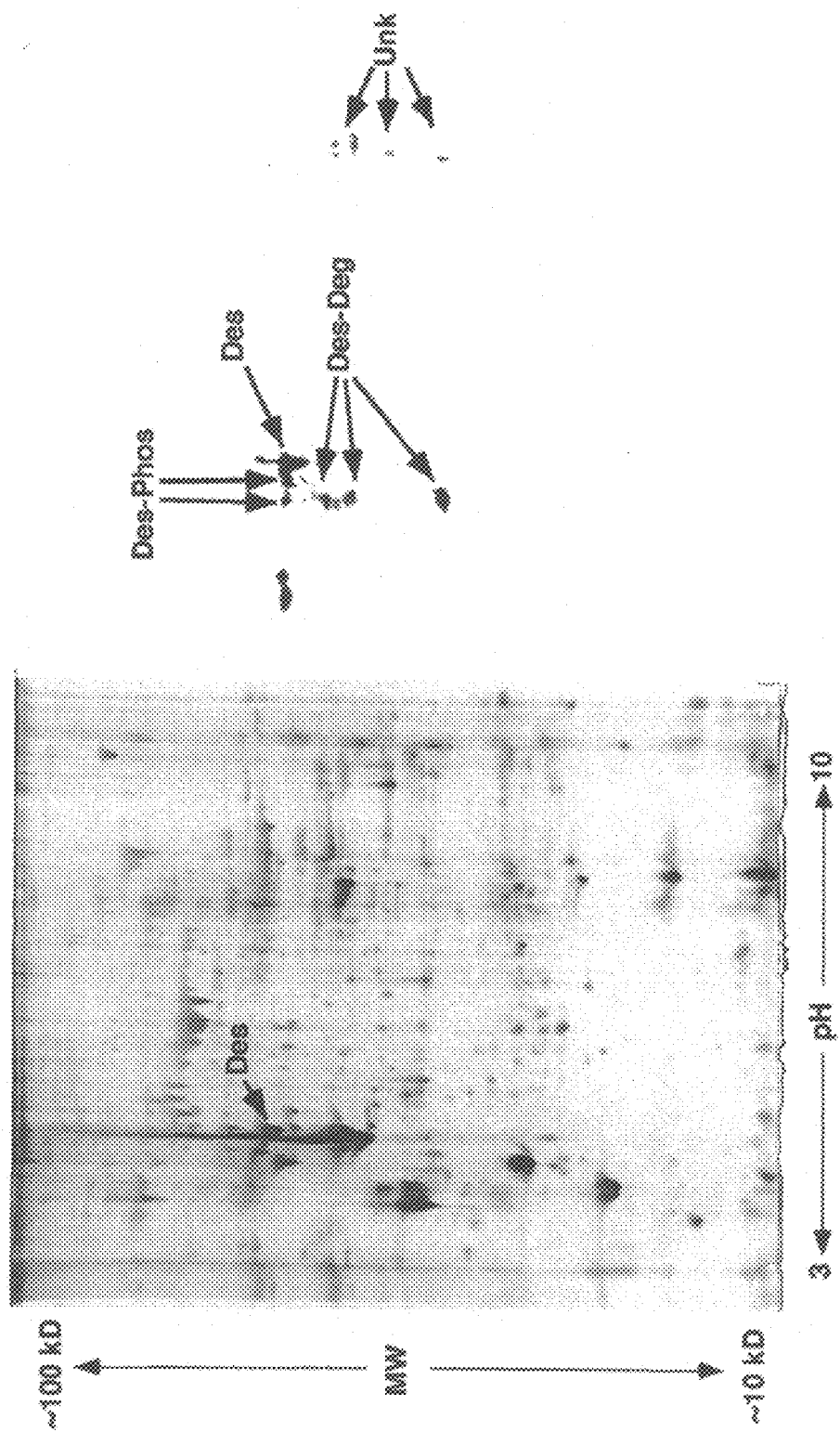
Figure 9:
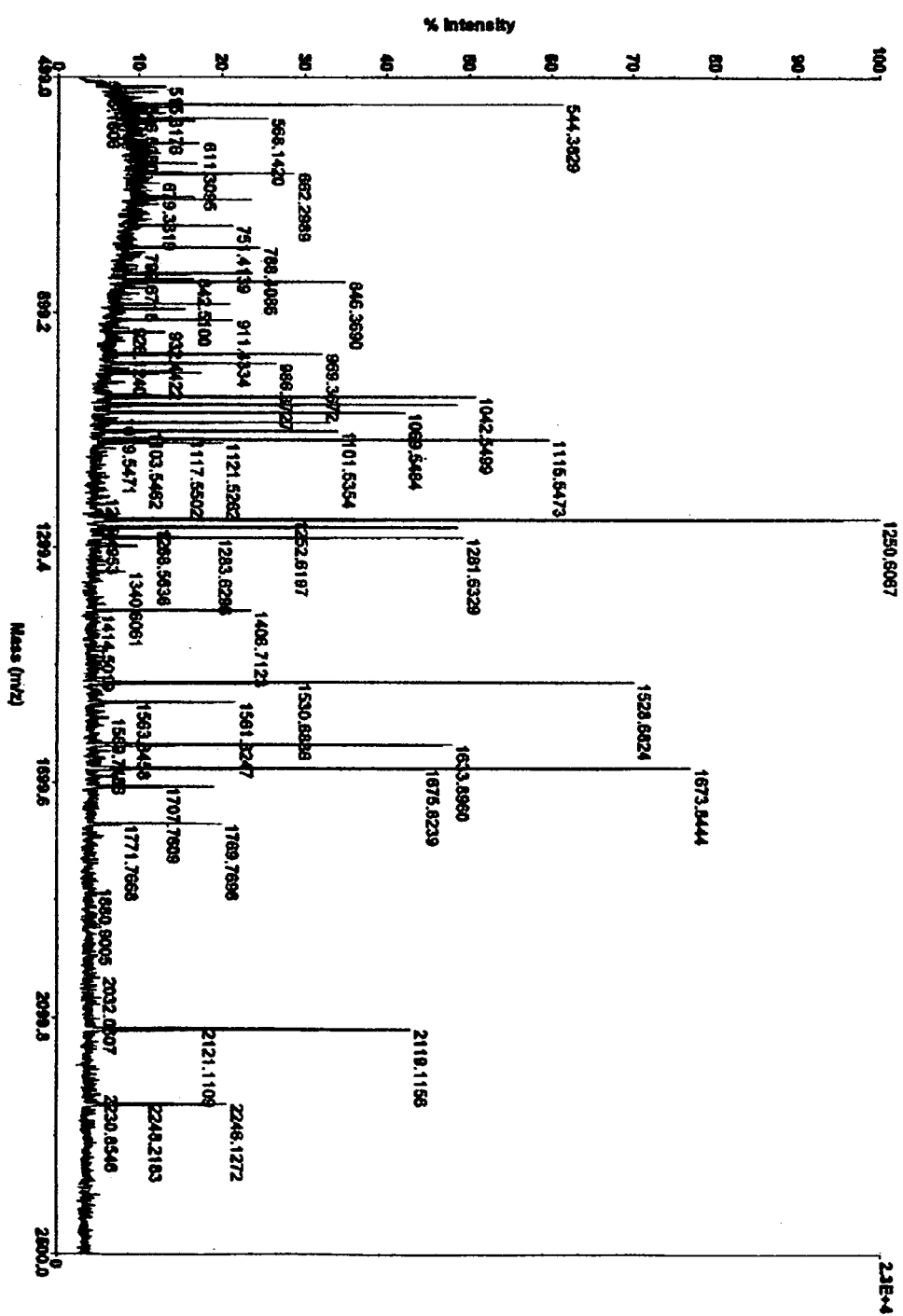

FIG. 9 represents an example of a spectrum obtained using MALDI-TOF on a trypsin digest of the protein spot identified as Des in FIGS. 7A, 7B, 8A and 8B. After identifying the monoisotopic peaks, the peptide molecular weights were entered into MS-FIT (http://prospector.ucsf.edu), with the following options selected: peptide mass tolerance 50 ppm; minimum 4 peptides to match; identity mode; cysteines modified by carbamidomethylation; possible phosphorylation of S, T, and Y; full pI range (3-10) and molecular weight range (1000-100,000 Da). This process confirmed the indicated protein to be desmin.

Figure 10:
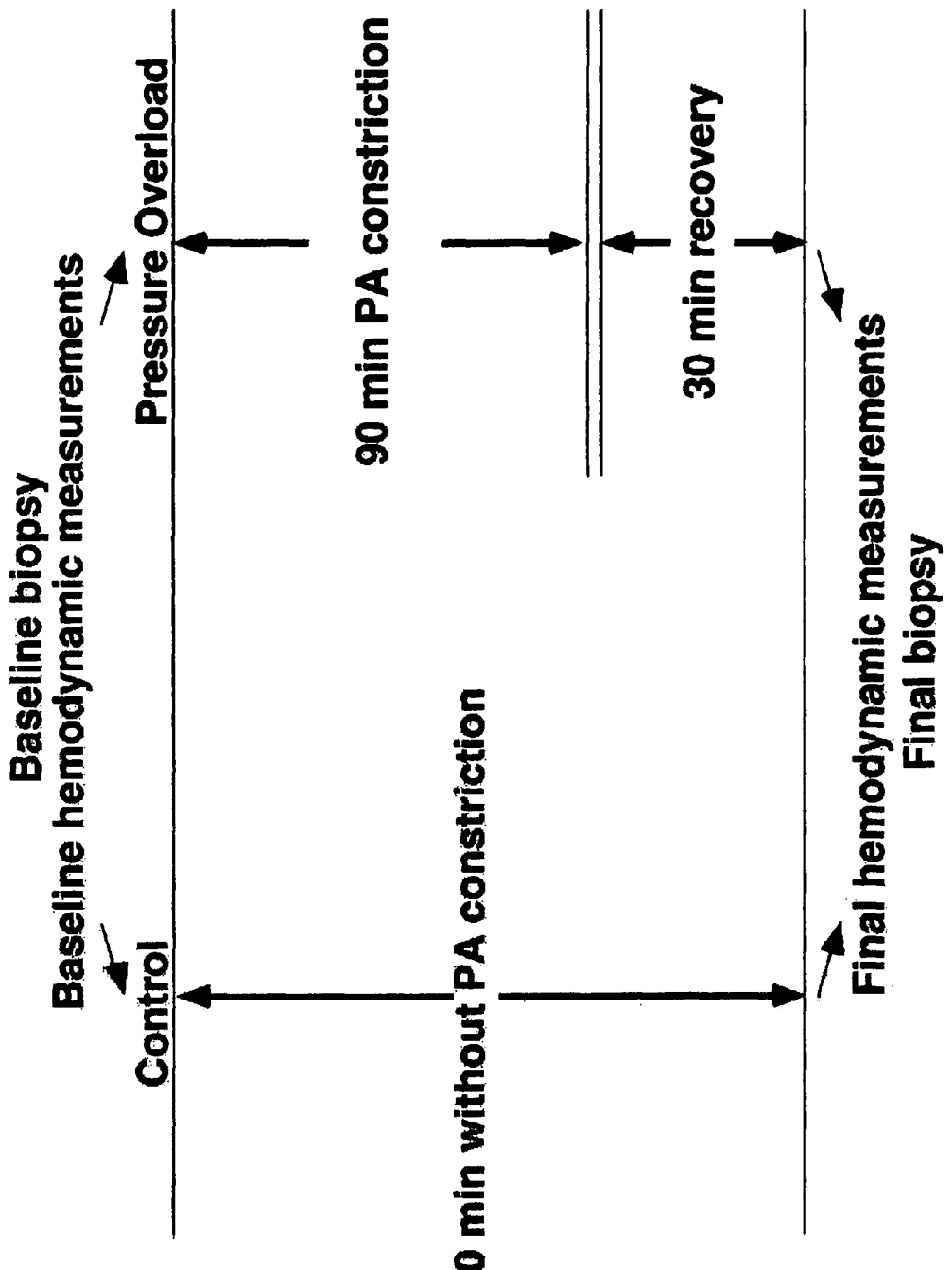

FIG. 10 illustrates an example of a flow chart of one experimental protocol. In these experiments, the total time elapsing from initial instrumentation and biopsy to final biopsy and hemodynamic measurements was kept constant to eliminate potential changes due solely to surgical and anesthetic stress.

Figure 11:
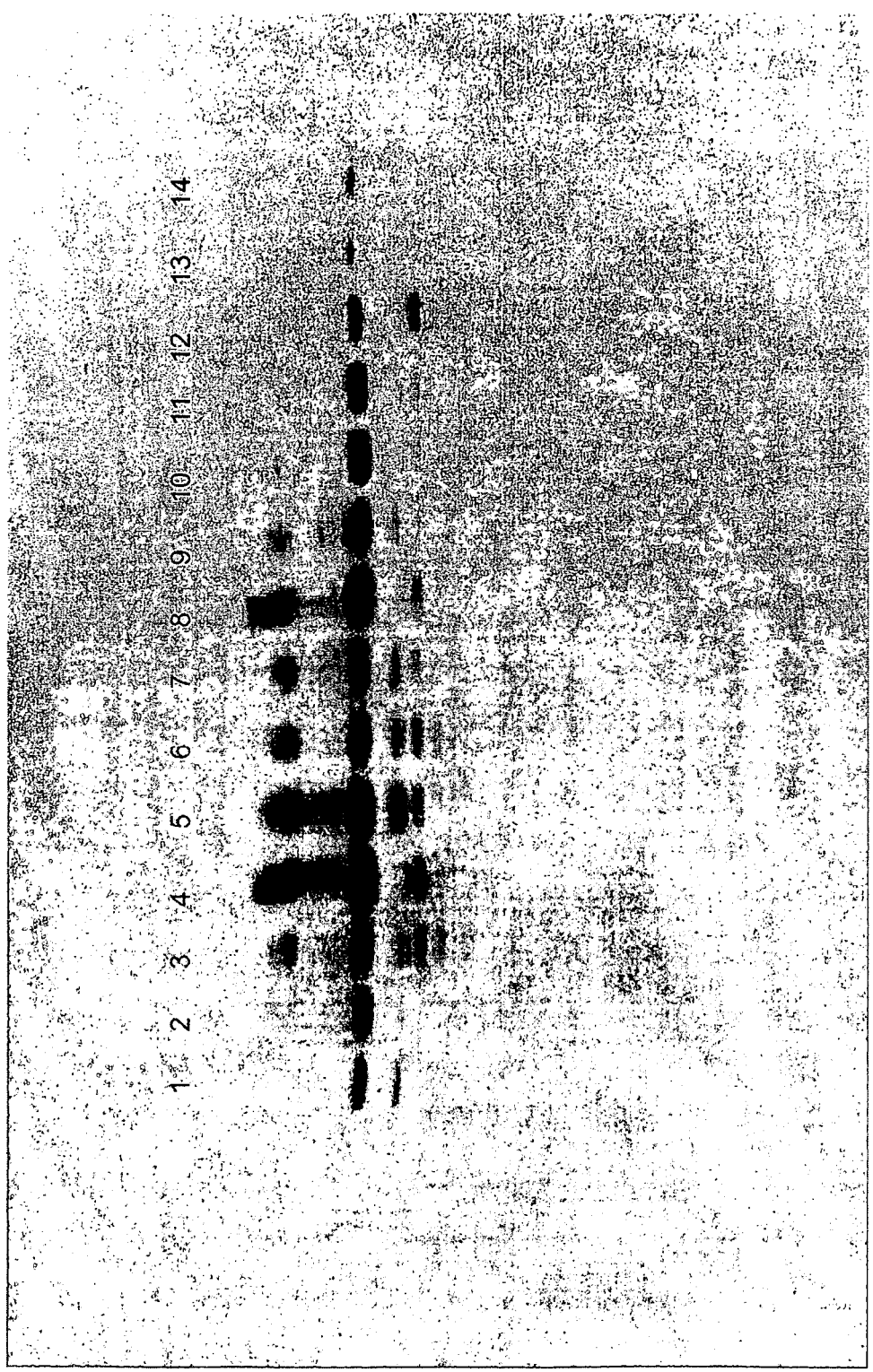

FIG. 11: illustrates an exemplary Western blot demonstrating an increase in myosin under various conditions.

Figure 12:
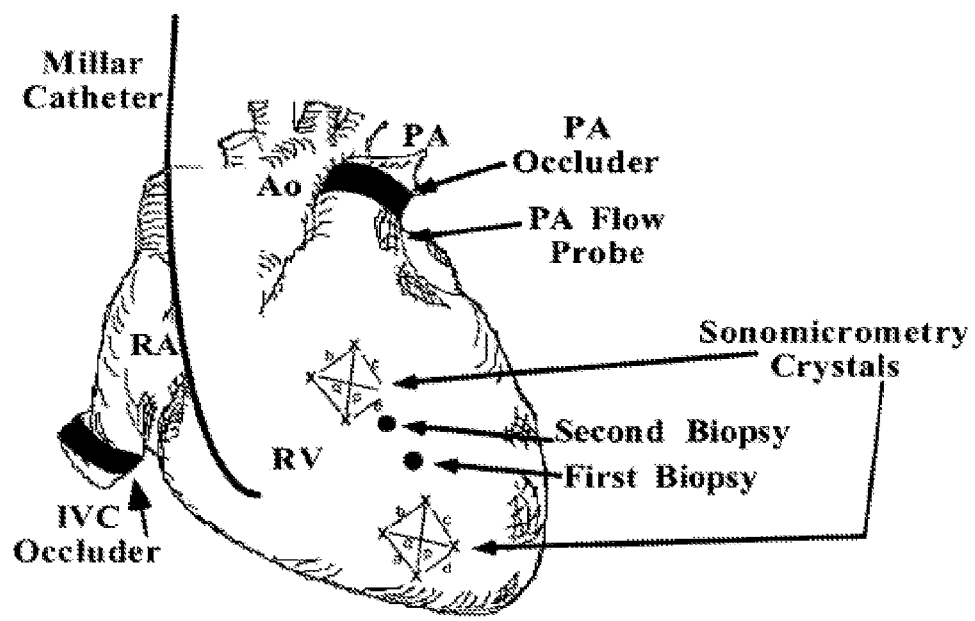

FIG. 12 shows a diagram of pig heart illustrating the experimental model.

DEFINITIONS

As used herein the specification, "a" or "an" may mean one or more. As used herein in the claim(s), when used in conjunction with the word "comprising", the words "a" or "an" may mean one or more than one. As used herein "another" may mean at least a second or more.

As used herein the specification, "attenuate" or "attenuates" or "attenuating" or "attenuation" may mean to lessen, become weaker, in strength, value, or magnitude for example "lessen the symptoms of". As used herein in the claim(s), the words "attenuate" or "attenuates" or "attenuating" may include but are not limited to "lessening the symptoms of" or may include but not limited to "curing a condition".

As used herein the specification, "subject" or "subjects" may include but are not limited to birds, reptiles or mammals such as domestic mammals for example dogs, cats, ferrets, rabbits, pigs, horses, or cattle. As used herein the specification, "subject" or "subjects" may include but are not limited to non-domestic mammals such as wild animals or zoo animals for example monkeys, tigers and elephants. As used herein the specification, "subject" or "subjects" may include but are not limited to human subjects.

DETAILED DESCRIPTION

In the following section, several embodiments of, for example, processes, compositions, devices and methods are described in order to thoroughly detail various embodiments. It will be obvious though, to one skilled in the art that practicing the various embodiments does not require the employment of all or even some of the specific details outlined herein. In some cases, well known methods or components have not been included in the description in order to prevent unnecessarily masking various embodiments.

General Considerations for Clinical Recovery from Acute RV Pressure Overload

Clinical recovery from acute RV pressure overload is correlated to some extent with success in alleviating the condition responsible for the pressure overload. However, it is the RV contractile dysfunction, not the pressure overload, that directly contributes to morbidity and mortality of subjects suffering from acute RV pressure overload. Thus, any factors that affect the development of or recovery from RV contractile dysfunction play direct and important roles in ultimate clinical outcome. However, there has been very little investigation of this phenomenon, and thus there is little information available to suggest possible therapeutic interventions for directly attenuating the development of RV contractile dysfunction from acute pressure overload.

RV stroke volume is depressed during acute RV pressure overload. Previously, it was assumed that this was a direct and reversible consequence of the increase in afterload, and it was unknown that there is an alteration in intrinsic RV contractile function due to the RV pressure overload.

Recent Advances in Acute RV Pressure Overload Research

Alteration in RV contractile function following RV pressure overload suggests that intrinsic alterations in RV contractile function contribute to RV failure during RV pressure overload as well. Understanding the mechanism of RV dysfunction from acute pressure overload suggests several potential strategies to prevent this phenomenon. The mechanism of RV dysfunction from pressure overload may be similar to mechanisms of muscle dysfunction in other settings. For example, prolonged or strenuous exercise causes skeletal muscle injury and dysfunction. While the exact mechanism of injury is uncertain, it has been established that the calcium-sensitive cysteine protease calpain is activated following strenuous skeletal muscle exercise, and that such activation is associated with degradation of several proteins, for example, myofibrillar and cytoskeletal proteins.(6)

Advances in investigation of acute RV pressure overload have demonstrated that intrinsic RV contractile function remains depressed after a period of pressure overload. This is observed even after complete restoration of normal loading conditions. The severity of RV dysfunction following pressure overload is directly related to the level of RV free wall stress during pressure overload.(7) While qualitatively similar to myocardial dysfunction of the left ventricle (LV), this contractile dysfunction following ischemia-reperfusion is likely not to be due to ischemia of the RV.(8)

Protease Involvement in Acute RV Contractile Function

Activation of calpain has also been hypothesized to contribute to myocardial dysfunction (stunning) following ischemia-reperfusion through proteolysis of the thin-filament regulatory protein troponin-I or through proteolysis of the myocyte cytoskeleton.(9, 10) Alternatively, some investigators have proposed that stunning is due to alterations in the extracellular collagen matrix (11).

Alteration in RV contractile function following RV pressure overload suggests that intrinsic alterations in RV contractile function contribute to RV failure during RV pressure overload. Several potential mechanisms may contribute to impaired contractile function due to acute RV pressure overload. RV dysfunction from pressure overload may be similar to mechanisms of muscle dysfunction in other settings. In one example, prolonged or strenuous exercise leads to skeletal muscle injury and dysfunction. Here, a calcium-sensitive cysteine protease, calpain, is activated following strenuous skeletal muscle exercise, and this activation is associated with degradation of several myofibrillar and cytoskeletal proteins (12) In one study, calpain has been indicated to contribute to myocardial dysfunction (stunning) following ischemia-reperfusion through proteolysis of the thin-filament regulatory protein troponin-I (13) or through proteolysis of the myocyte cytoskeleton (14). Alternatively, another possibility is that changes in contractile function as a result of acute RV pressure overload may be due to alterations in the extracellular collagen matrix (15). Another possibility is that myofibrils may be released from myocytes or degraded as occurs in sepsis (16).

One potential mechanism of RV dysfunction in acute RV pressure overload is impaired myosin function from stress-induced myosin glycosylation.(67) Alterations in calpain-like proteases can alter sensitivity to glycosylation in some model systems.(68)

Protease Inhibition and Contractile Dysfunction

In the present invention, methods and compositions to treat heart failure are disclosed. More specifically, right heart failure due to acute or chronic pressure overload may be prevented and/or treated. Provisional U.S. patent application Ser. No. 60/548,801 is incorporated by reference herein in its entirety. In one embodiment, a patient may be treated with a protease inhibitor alone or in combination with other treatments. In one embodiment, a cysteine protease such as calpain contributes to RV dysfunction by causing proteolysis of contractile or regulatory proteins and one or more of these protasase may be inhibited. In one embodiment, inhibition of one or more cysteine proteases may be used to attenuate the development of contractile dysfunction during a process such as acute or chronic RV pressure overload. One benefit may be that the treatment may reduce or eliminate contractile dysfunction. In another embodiment, stress activation of matrix metalloproteinases contributes to RV dysfunction by degrading the extracellular matrix. In yet another embodiment, inhibition of matrix metalloproteinases may be used to attenuate the development of contractile dysfunction during acute or chronic RV pressure overload.

Acute right ventricular (RV) pressure overload, resulting from massive pulmonary embolism, hypoxic pulmonary vasoconstriction, or following cardiopulmonary bypass or cardiac transplantation, may lead to RV failure; such RV failure is an important cause of morbidity and mortality in patients with these conditions. RV failure is a leading cause of early mortality in patients undergoing cardiac transplantation, and often requires inotropic support or ventricular assist devices. It has been demonstrated herein that RV dysfunction following pressure overload persists despite restoration of baseline loading conditions. Data herein suggests that proteases, for example, a cysteine protease, may contribute to this dysfunction.

Prior Treatment

There is currently no pharmaceutical-based therapeutic strategy for prevention or treatment of right heart failure due to pressure overload other than standard strategies to reduce right heart pressure; these strategies are often unsuccessful or result in serious complications. Other investigators have shown that cysteine protease inhibition may attenuate skeletal muscle dysfunction from excessive stress, and left ventricular dysfunction from ischemia.

Treatment of acute RV contractile failure is currently limited to alleviation of underlying conditions responsible for acute pressure overload. However, such measures are often ineffective. There is currently no specific therapy for acute RV contractile dysfunction. Therefore, development and use of specific inhibitors of cysteine proteases or MMPs may be used therapeutically in these conditions to directly target acute RV contractile dysfunction.

Right heart failure from acute pressure overload may be an anticipated complication of cardiac surgical procedures, blood clots to the lungs (pulmonary emboli), and respiratory failure. Right heart failure likely contributes directly to at least 60,000 deaths per year in the United States. Pharmaceutical manufacturers are likely to be interested in development and application of a cysteine protease and/or matrix metalloproteinase inhibitors for this purpose. There is currently no agent indicated for prevention of right ventricular contractile dysfunction, and cysteine protease inhibitors are not yet known to be used therapeutically for any purpose.

The rationale for use of protease inhibitors is based on the possible mechanisms of RV contractile dysfunction due to pressure overload. Herein, these potential mechanisms of contractile dysfunction are categorized as defects in force generation or defects in force transduction.

Defects in Force Generation

Some evidence indicates that reduced calcium responsiveness of stunned myocardium is due to modification of myofibrillar proteins. For example, isolated rat hearts subjected to global ischemia-reperfusion exhibit degradation of the thin-filament regulatory protein troponin-I (TnI), with appearance of a 26 kDa TnI fragment. (17) Moreover, transgenic mice over-expressing the 26 kDa fragment of TnI exhibit morphologic and functional characteristics similar to those observed in ischemia-reperfusion, while TnI isolated from regionally stunned porcine LVs results in decreased myofilament sensitivity when reconstituted with normal skeletal muscle.(18, 19).

Degradation of TnI has not, however, been identified in all models of stunning. In one example, pigs subjected to total coronary occlusion or graded ischemia and reperfusion may exhibit severe reductions in contractile function with no evidence of TnI degradation, and ischemic stunning occurs without TnI degradation when elevation of preload is prevented. (20)

Cytoskeletal Proteins.

One alternative mechanism of stunning in ischemia-reperfusion may be degradation of cytoskeletal proteins responsible for force transduction. Desmin and α-actinin are associated with the sarcomere Z-line, and are believed to participate in mechanical coupling of sarcomeres; spectrin is thought to participate in mechanically coupling the sarcomere to the sarcolemma. If these proteins are altered in any way, this could potentially result in a reduction of maximum calcium activated force development without a corresponding defect in myofibrillar ATPase activity. Degradation of desmin has been found in isolated rat hearts following ischemia-reperfusion, and in isolated myocytes following treatment with a cysteine protease.(21) This degradation was associated with a reduction in maximum calcium activated isometric force development, reduced calcium-sensitivity of isolated myocytes, and disruption of the normal Z-line arrangement.

Other investigators have also reported degradation of desmin, spectrin and/or α-actinin following ischemia-reperfusion. Thus, it is likely that the degradation and or change in compartmentalization of these proteins play a role in the contractile dysfunction of acute RV pressure overload.

Pressure overload in the RV is analogous to strenuous exercise in skeletal muscle. It is well established that strenuous or prolonged exercise may cause skeletal muscle injury and dysfunction. Numerous investigations have shown that strenuous exercise results in degradation of myofibrillar and cytoskeletal proteins in skeletal muscle, accompanied by characteristic morphologic changes including sarcomeric Z-line disruption, mitochondrial swelling, and sarcoplasmic reticulum vacuolization. Such morphologic changes correlate with reduced tension development.(22)

Currently, there is little or no data on alterations in RV myocardial ultrastructure following acute pressure overload; however, alterations in cytoskeletal architecture in RV myocardium have been identified in newborn calves with chronic pulmonary hypertension and RV failure due to chronic hypoxia.(23) In addition, rabbits subjected to acute LV pressure overload by aortic constriction for 45 min manifest disruption of sarcomere Z-lines, myofibrillar degeneration, contraction zones, and altered passive pressure-length relationships. These ultrastructural abnormalities are similar to those found in skeletal muscle following strenuous exercise. It is likely that degradation of cytoskeletal proteins and/or disruption of sarcomere architecture are associated with RV dysfunction after pressure overload.

Cysteine Protease Inhibitors

A broad list of inhibitors is commercially available from suppliers such as Calbiochem. In one embodiment, MDL28170 (Calpain Inhibitor III, carbobezoxy-valinyl-phenylalaninal, Z-Val-Phe-CHO, $C_{22}H_{26}N_2O_4$, CAS Number 88191-84-8) an inhibitor of calpain may be used to attenuate RVPO. Several advantages of MDL28170 are that it is membrane permeable, relatively selective, potent, and inexpensive. It is a potent, cell-permeable inhibitor of calpain I and II (K i=8 nM).

In one embodiment, a cysteine protease inhibitor may be used to prevent degradation of certain cytoskeletal proteins that play a role in contractile function during acute RV pressure overload. In another embodiment, MDL 28170 may be used as a cysteine protease inhibitor to prevent degradation of certain cytoskeletal proteins that play a role in contractile function during acute RV pressure overload. MDL28170 is a synthetic inhibitor of calpain that was demonstrated to protect rat erythrocyte membrane-associated cytoskeletal proteins from proteolytic degradation (IC50=1 microM) which occurs when the cells are rendered permeable to calcium.

SJA6017, Another Cysteine Protease Inhibitor

In another study, the peptide aldehyde SJA6017, N-(4-fluorophenylsulfonyl)-L-valyl-L-leucinal, a synthetic agent, was used to characterize its effect on preventing calcium ionophore-induced cataracts in cultured rat lenses. In vitro introduced SJA6017 demonstrated strong inhibition of purified m-calpain from porcine kidney. Casein zymography confirmed that SJA6017 reversibly bound to the active site of m-calpain. SJA6017 was also confirmed to be a cell-permeable inhibitor in Molt-4 cells. In cultured lenses, SJA6017 reduced nuclear opacity and proteolysis of crystallins and alpha-spectrin caused by calcium ionophore A23187. These results suggested that SJA6017 is a reversible and cell-permeable cysteine protease inhibitor that may possess great efficacy against calcium-induced models of cataract. In one embodiment of the present invention, SJA6017 may be used alone or in combination with other cysteine protease inhibitors to attenuate, treat or prevent contactile dysfunction in a subject having or developing acute pressure overload.

Other Studies

The initial investigation of intrinsic RV dysfunction due to acute pressure overload characterized the phenomenon and explored potential mechanisms such as ischemia or the release of humoral factors. A subsequent investigation identified the specific hemodynamic variables that predict the severity of RV dysfunction following acute pressure overload. (24, 25)

Several approaches to identifying the mechanism of RV dysfunction from pressure overload have been considered: 1) identification of ultrastructural changes in RV myocardium subjected to pressure overload; 2) assessment of alterations in myofibrillar ATPase in RV myocardium subjected to pressure overload; 3) identification of altered content, degradation and/or phosphorylation of important contractile, sarcomeric regulatory and cytoskeletal proteins in porcine myocardium; 4) measurement of matrix metalloproteinase (MMP) and tissue inhibitors of MMP activity (TIMPs) in RV myocardium after pressure overload; 5) identification of regional heterogeneity in the response of RV myocardium to acute pressure overload; and 6) intracoronary administration of a specific cysteine protease inhibitor to directly test the hypothesis that cysteine protease activation contributes to RV contractile dysfunction after acute pressure overload (see Examples section).

Calpain and Degradation of Myofibrillar and Cytoskeletal Proteins.

There is evidence that calpain, a ubiquitous, non-lysosomal cysteine protease, may play a role in the genesis of contractile dysfunction. Calpain exists in two forms, designated μ-calpain and m-calpain because of the micromolar and millimolar levels of intracellular calcium required for their activation. The numerous intracellular substrates for calpain include the myofibrillar proteins troponin, tropomyosin and myosin light chain kinase; the cytoskeletal proteins desmin, α-actinin, vimentin, spectrin, integrin and cadherin; and soluble and membrane associated enzymes such as protein kinase A (PKA), protein kinase C (PKC), and phospholipase C. Calpain proteolysis typically occurs at specific sites, resulting in large fragments, some of which are metabolically active.(26)

While typical intracellular calcium levels were previously thought to be insufficient for activation of μ-calpain (the calpain isoform most sensitive to calcium activation), evidence now exists that mild elevations in intracellular calcium levels (such as may occur following brief ischemia-reperfusion) are sufficient for calpain activation in vivo. (27) Moreover, proteolysis of calpain's substrates is dependent on both the activation of calpain itself, and on modifications of the substrates. For example, phosphorylation of troponin by PKA or PKC alters its sensitivity to degradation by calpain. Thus, superphysiologic levels of intracellular calcium may not be necessary for proteolysis by calpain.

Since several major muscle cytoskeletal and myofibrillar proteins are potential substrates for calpain, calpain activation has been hypothesized to play a role in skeletal muscle damage after exercise, and in the genesis of myocardial stunning following ischemia-reperfusion. Calpain activity increases in rat skeletal muscle following prolonged exercise, along with loss of desmin and α-actinin.(28)

Other investigators have shown that the synthetic calpain inhibitor-1 attenuates cytoskeletal degradation and myocardial stunning in isolated rat hearts subjected to global ischemia. Finally, inhibition of calpain by calpeptin prevented TnI degradation and stunning due to elevated LV end-diastolic pressure without ischemia in isolated rat hearts. (29) In one embodiment, at least one inhibitor of a cysteine protease may be administered to a subject suspected of experiencing RVPO. In another embodiment, at least one inhibitor of calpain, for example calpain-1, may be administered to a subject suspected of experiencing RVPO to attenuate or prevent development of RV contractile dysfunction.

Alterations of the Extracellular Collagen Matrix.

In contrast to the LV, the RV has evolved as a low-pressure pump, and the RV may dilate during acute RV pressure overload. Since ECM disruption may occur in isolated rat LVs passively dilated by markedly elevated intracavitary pressure, it is possible that mechanical disruption of the ECM consequent to severe RV dilatation could contribute to RV dysfunction. However, in one model of RV dysfunction due to acute pressure overload, diastolic dilatation is mild, and diastolic RV pressure during acute RV pressure overload (average 7-8 mmHg) is far below the diastolic intracavitary pressures that resulted in matrix disruption in isolated rat hearts (100-120 mmHg).(30) Moreover, even when RV dilatation was prevented entirely by pericardial constraint, RV dysfunction still occurred following acute pressure overload.(31)

Alteration of the extracellular collagen matrix (ECM) due to altered activity of matrix metalloproteinases has been demonstrated to contribute to myocardial remodeling and heart failure.(32) Some investigators have hypothesized that alterations in the ECM with consequent defects in force transduction also contribute to stunning acutely following ischemia-reperfusion. In one example, cardiomyocytes isolated from hearts following ischemic stunning did not manifest contractile abnormalities, suggesting that the contractile defect was extracellular, although these results conflict with others. Finally, acute pressure overload has been shown to cause activation of MMPs in dog hearts in vivo, and excessive exercise may activate MMPs in skeletal muscle.(34) It is possible that acute RV pressure overload might also result in MMP activation that in turn might contribute to the development of RV contractile dysfunction.

Mechanism of RV Dysfunction after Acute Pressure Overload.

Figure 4:
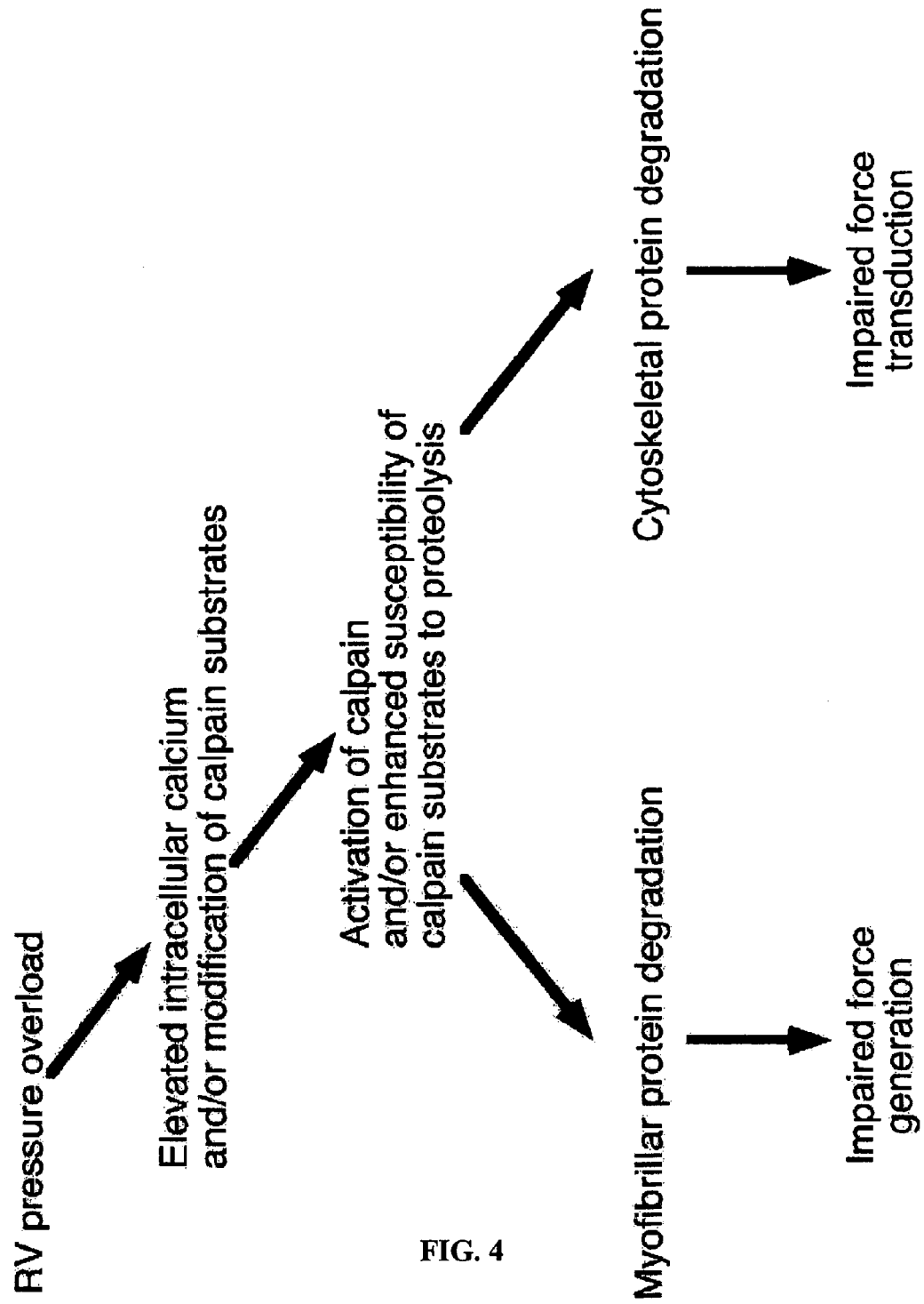
FIG. 4 Illustrates an exemplary cascade of the hypothesized mechanism of RV contractile dysfunction following acute pressure overload.

One possible mechanism of RV dysfunction following acute RV pressure overload is illustrated in FIG. 4: acute RV pressure overload results in elevated intracellular calcium with activation of calpain, and/or phosphorylation or other modification of calpain's substrates resulting in their greater susceptibility to calpain-mediated degradation. Proteolytic degradation of cytoskeletal proteins then impairs sarcomeric force transduction; or, proteolytic degradation of myofibrillar regulatory proteins then causes impaired calcium responsiveness of myofibrillar ATPase activity and reduced force generation. Alternatively, stress-induced activation of MMPs may cause degradation of the ECM, basement membrane, or other regulatory proteins with impaired force transduction or production.

Matrix Metalloproteinase Inhibitors

As members of a zinc-containing endoproteinase family, the MMPs have structural similarities, but each enzyme has a different substrate specificity, may be produced by different cells, and may have different induceabilities. One important structural component destroyed by MMPs is the extracellular matrix (ECM). The ECM is a complex structural entity surrounding and supporting cells that are found within mammalian tissues. The ECM is composed of 3 major classes of biomolecules; structural proteins: for example collagen and elastin, specialized proteins, for example fibrillin, fibronectin, and laminin; and proteoglycans: these are composed of a protein core to which is attached long chains of repeating disaccharide units termed of glycosaminoglycans (GAGs) forming extremely complex high molecular weight components of the ECM. Collagen is the principal component of the ECM, and MMPs induce ECM degradation and affect collagen deposition. Inhibitors of MMP(s) exist and some of these inhibitors are tissue specific. It was previously demonstrated that acute pharmacological inhibition of MMPs (or in some cases a deficiency in MMP-9) attenuated left ventricle dilatation in infarcted mouse hearts. Endogenous inhibitors of MMPs are referred to as tissue inhibitors of metalloproteinases (TIMPs). Synthetic forms of MMPIs also exist, for example GM6001 (galardin, Calbiochem), GM2487 (galardin derivative, Calbiochem), Prinomastat (AG3340), Marimastat (BB-251), and Metastat (COL-3). It was previously shown that MMPIs reduce pathologic remodeling in the left ventricle in rabbits. In addition, this study also demonstrated that MMPI increases rather than decreases neovascularization in the subendocardium. These enzymes have also been shown to degrade troponin and myosin.

In one embodiment, MMPIs may be administered to treat and/or prevent RV pressure overload induced RV contractile dysfunction due to acute RV pressure overload. In another embodiment, the MMPIs may include the following TIMPs including but not limited to TIMP-1, TIMP-2, TIMP-3 and TIMP-4 in combination with introducing any other agent such as an inhibitor of cysteine proteases to treat and/or prevent RV pressure overload induced RV contractile dysfunction. In another embodiment, naturally occurring inhibitors of MMPs may be increased by exogenous administration of recombinant TIMPs to treat and/or prevent RV pressure overload induced RV contractile dysfunction. In one embodiment, MMPI agents will be introduced systemically to treat and/or prevent RV pressure overload induced RV contractile dysfunction. In one embodiment, MMPI agents will be introduced to the affected part of the heart by multiple injections to the infarct region during an open chest procedure or via a minimally invasive procedure. In addition, the MMPI agents may be introduced via suspension or sustained release formula, for example introduced in microparticles. In one embodiment, the introduction of MMPIs may precede, coincide or follow any other treatment to treat and/or prevent RV pressure overload induced RV contractile dysfunction.

Methods

Antibodies Uses

Means for preparing and characterizing antibodies are well known in the art (See, e.g., Antibodies: A Laboratory Manual, Cold Spring Harbor Laboratory, 1988; incorporated herein by reference).

In certain embodiments, it may be desirable to make monoclonal antibodies against targeted cysteine proteases (eg. calpain). The appropriate protease, or portions thereof, may be coupled, bonded, bound, conjugated, or chemically-linked to one or more agents via linkers, polylinkers, or derivatized amino acids. This may be performed such that a bispecific or multivalent composition or vaccine is produced. It is further envisioned that the methods used in the preparation of these compositions are familiar to those of skill in the art and should be suitable for administration to human subjects, i.e., pharmaceutically acceptable. Preferred agents are the carriers keyhole limpet hemocyanin (KLH) or bovine serum albumin (BSA).

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

Phage Display

The methods described herein for identification of targeting peptides involve the in vivo administration of phage display libraries. In various embodiments of the invention, proteins may be identified and then used to generate monoclonal antibody producing immortalized splenocytes as therapeutic and/or diagnostic targets. Various methods of phage display and methods for producing diverse populations of peptides are well known in the art. For example, U.S. Pat. Nos. 5,223,409, 5,622,699 and 6,068,829, each of which is incorporated herein by reference and describe methods for preparing a phage library. The phage display technique involves genetically manipulating bacteriophage so that small peptides can be expressed on their surface (Smith et al, 1985, 1993). The potential range of applications for this technique is quite broad, and the past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence.

Proteins and Peptides

In certain embodiments, the invention concerns novel compositions comprising at least one protein or peptide that may be used as an antigen for monoclonal antibody production for use in prevention and or treatment of RV pressure overload induced RV contractile dysfunction. As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide are used interchangeably herein.

In certain embodiments the size of the at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | Aile | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

Peptide Mimetics

Another embodiment for the preparation of polypeptides according to the invention is the use of peptide mimetics for monoclonal antibody production. Mimetics are peptide-containing molecules that mimic elements of protein secondary structure. See, for example, Johnson et al, "Peptide Turn Mimetics" in BIOTECHNOLOGY AND PHARMACY, Pezzuto et al., Eds., Chapman and Hall, New York (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics.

Fusion Proteins

Other embodiments of the invention concern fusion proteins. These molecules generally have all or a substantial portion of a targeting peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In preferred embodiments, the fusion proteins of the instant invention comprise a targeting peptide linked to a therapeutic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually and protein or peptide could be incorporated into a fusion protein comprising a targeting peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

Protein Purification

In certain embodiments a protein or peptide such as desmin or troponin may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, HPLC (high performance liquid chromatography) FPLC (AP Biotech), polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. One of the more efficient methods of purifying peptides is fast performance liquid chromatography (AKTA FPLC) or even HPLC.

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification are well known to those of skill in the art. These include, for example, precipitation with ammonium sulfate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Synthetic Peptides

Because of their relatively small size, the targeting peptides of the invention can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, usually from about 6 up to about 35 to 50 amino acids, can be readily synthesized by such methods. Alternatively, recombinant DNA technology may be employed wherein a nucleotide sequence which encodes a peptide of the invention is inserted into an expression vector, transformed or transfected into an appropriate host cell, and cultivated under conditions suitable for expression.

siRNA

In one embodiment of the present invention, siRNA may be directed toward one or more cysteine proteases for targeting one or more proteases. In another embodiment, one or more siRNAs may be used to reduce or silence at least one cysteine protease target gene in a subject having or developing RV contractile failure from acute pressure overload. Small interfering RNAs (siRNAs) are short RNA molecules (typically from 21 to 23 nucleotides in length) that may be used to induce targeted gene silencing by RNA interference.(35, 36, 37) SiRNAs occur naturally in vivo when double-stranded RNA is cleaved by ribonuclease III to produce a short siRNA sequence. Synthetic siRNAs may also be introduced into cells to inhibit expression of one or more selected genes. SiRNAs may be generated by standard solid-phase oligonucleotide synthesis, by RNA-specific endonuclease cleavage of double-stranded RNA, or by expression of transfected DNA templates incorporating promoter sequences for RNA polymerase III. Introduction of siRNA into a mammalian cell results in the targeted destruction of messenger RNAs of the same sequence. Commercial products for siRNAs are available from a number of sources, such as Gene Therapy Systems, Inc. (San Diego, Calif.), Promega (Madison, Wis.) and Sirna Therapeutics (Boulder, Colo.).

Methods for design of siRNA sequences are publicly available. For example, the siRNA Target Finder may be used online at the Ambion website. Target mRNA sequences are input into the program, which then scans for 21 nucleotide sequences that begin with an AA dinucleotide. The program selects for siRNAs with about a 30 to 50% GC content, avoiding sequences with 4-6 polyT stretches that would function as terminators for RNA Polymerase III transcription. After selection of two to four siRNA candidates, the generated sequences may be searched for homology (for example, using the BLAST search engine on the NCBI server) to other untargeted mRNA sequences. SiRNAs with homology to non-targeted sequences are eliminated from consideration. SiRNA expression cassettes may also be obtained from Ambion (Austin, Tex.). SiRNAs may be purchased and used according to the manufacturer's instructions to provide targeted inhibition of the expression of specific genes, such as calpain or other cysteine proteases.

Dosages

In one embodiment, any of the described agents may be introduced in one or more doses in a volume of about 1 µl to 1 liter. In another embodiment, any of the described agents may be introduced in one or more doses in a volume of about 1 µl to 500 mls. In another embodiment, any of the described agents may be introduced in one or more doses in a volume of about 1 µl to 100 µl. In a preferred embodiment, the any of the described agents may be introduced in one or more doses in a volume of about 1 µl to 50 µl.

In one embodiment, any of the described agents may be introduced in one or more doses in tablet, pill, powder or gel form for oral, nasal, rectal or other systemic administrative form. In another embodiment, any of the described agents may be introduced in one or more appropriate doses depending on the disease condition and physiological makeup of the subject.

In alternate embodiments, the treatment volume may be larger (eg. intravenous pressure perfusion (IV) route). These volumes may range from about 2 mls to about 250 mls. Alternatively, these volumes may range from about 2 mls to about 100 mls. In other embodiments, these volumes may range from about 2 mls to about 30 mls.

Delivery Systems

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,102,926, 6,120,520, 6,251,104, 6,309,370; 6,432,119; 6,485,481). The delivery device may include an apparatus for intracardiac drug administration, including a sensor for positioning within the heart, a delivery device to administer the desired agent and amount at the site of the position sensor. The apparatus may include, for example, a catheter body capable of traversing a blood vessel and a dilatable balloon assembly coupled to the catheter body comprising a balloon having a proximal wall. A needle may be enclosed within the catheter body and includes a lumen having dimensions suitable for a needle to be advanced there through. The needle body includes an end coupled to the proximal wall of the balloon. The apparatus also includes an imaging body enclosed within the catheter body and including a lumen having a dimension suitable for a portion of an imaging device to be advanced there through. The apparatus may further include a portion of an imaging device disposed within the imaging body adapted to generate imaging signal of the infarct region within the ventricle. The apparatus may be suitable for accurately introducing a treatment agent at a desired treatment site.

In another embodiment a needle catheter used to deliver the agent to the ventricle for example, a dysfunctional region, may be configured to include a feedback sensor for mapping the penetration depth and location of the needle insertion. The use of a feedback sensor provides the advantage of accurately targeting the injection location. Depending on the type of agent administered, the target location for delivering the agent may vary. For example, one agent may require multiple small injections within a dysfunctional region where no two injections penetrate the same site.

In other embodiments, the catheter assembly may include a maneuverable instrument. This catheter assembly includes a flexible assembly. The catheter assembly may be deflectable and includes a first catheter, a second catheter, and a third catheter. The second catheter fits coaxially within the first catheter. At least one of the first catheter and the second catheter include a deflectable portion to allow deflection of that catheter from a first position to a second position, and the other of the first catheter and second catheter includes a portion which is preshaped (e.g. an angled portion formed by two segments of the angled portion). The third catheter has a sheath and a medical instrument positioned within the sheath. The third catheter fits coaxially within the second catheter. In another embodiment, a stabilizer, such as a donut shaped balloon, is coupled to a distal portion of the third catheter. Each catheter is free to move longitudinally and radially relative to the other catheters. The catheter assembly may be used but not limited to the local delivery of bioagents, such as cells used for cell therapy, one or more growth factors for fibroblast retention, or vectors containing genes for gene therapy, to the left ventricle. In one embodiment, the catheter assembly described may be used in delivering cell therapy for heart failure or to treat one or more portions of the heart that are ischemic. The catheter assembly uses coaxially telescoping catheters at least one or more being deflectable, to position a medical instrument at different target locations within a body organ such as the left ventricle. The catheter assembly may be flexible enough to bend according to the contours of the body organ. The catheter assembly may be flexible in that the catheter assembly may achieve a set angle according to what the medical procedure requires. The catheter assembly will not only allow some flexibility in angle changes, the catheter assembly moves in a three coordinate system allowing an operator greater control over the catheter assembly's movement portion of the second catheter, allowing for the distal tip of the third catheter to be selectively and controllably placed at a multitude of positions. It will be appreciated that the deflectable portion may alternatively be on the second catheter and the preshaped portion may be on the first catheter.

Various methods described herein can be used as a stand-alone injection needle/catheter during a surgical procedure such as an open heart surgery (e.g., coronary artery bypass graft (CABG)) procedure in which areas of the heart may be treated with, for example, growth factors for affecting therapeutic angiogenesis, or incorporated into a catheter-based system to access locations that are commonly used in percutaneous translumenal coronary artery (PTCA) procedures. The apparati (devices) and methods may similarly be used in other surgical procedures such as cancer-related procedures (e.g., brain, abdomen, or colon cancer procedures or surgeries). Additionally, various apparati (devices) and methods described herein can be used in conjunction with various catheter-related or endoscopic procedures that generally require minimal invasiveness to deliver a specific drug or growth factor into tissue. Examples of such procedures include, but are not limited to, orthoscopic surgery for joints (e.g., knee), laparoscopic surgery for the abdomen, and thoroscopic procedures related to chest injuries or treatments.

In another embodiment, a method may include introducing a treatment agent in a sustained release composition. The preferred period for sustained release of one or more agents is for a period of one to twelve weeks, preferably two to eight weeks. Methods for local delivery of sustained release agents include but are not limited to percutaneous devices for example intraventricular (coronary) or intravascular (coronary and periferal) devices.

EXAMPLES

Pig Model

In several experiments presented, a pig is used as a model for acute RV pressure overload. A major advantage of an in situ pig model of acute RV contractile dysfunction is its direct analogy to common clinical settings, and pigs are physiologically similar to humans. It also provides the unique potential to perform serial biopsies of the RV free wall, and to account for the heterogeneity of response to stress across the RV free wall that has been reported clinically.(38)

Example 1

Effect of Cysteine Protease Inhibition

RV contractile dysfunction due to acute pressure overload may be caused by activation of cysteine protease(s), leading to proteolytic degradation of cytoskeletal or myofibrillar proteins. To directly test this hypothesis, pigs were treated with the membrane-permeable cysteine protease inhibitor MDL-28170 (n=7) or DMSO/phosphate buffered saline vehicle (n=6) by direct infusion into the proximal right coronary artery, as described in the Methods under Protocol #2. Pigs were subjected to RV pressure overload by constriction of the main pulmonary artery for 90 min (mean PASP 63 mmHg), followed by 30 min recovery. MDL-28170 had no independent hemodynamic effects and did not alter the regional Frank-Starling relation under baseline conditions. However, MDL-28170 attenuated RV dysfunction resulting from acute RV pressure overload (RVPO) by more than 50%: thirty min after release of pulmonary artery constriction, preload-adjusted external work of the RV free wall was 69% of baseline in MDL-28170 treated pigs, but only 29% of baseline in vehicle-treated pigs (p<0.05).

Figure 1:
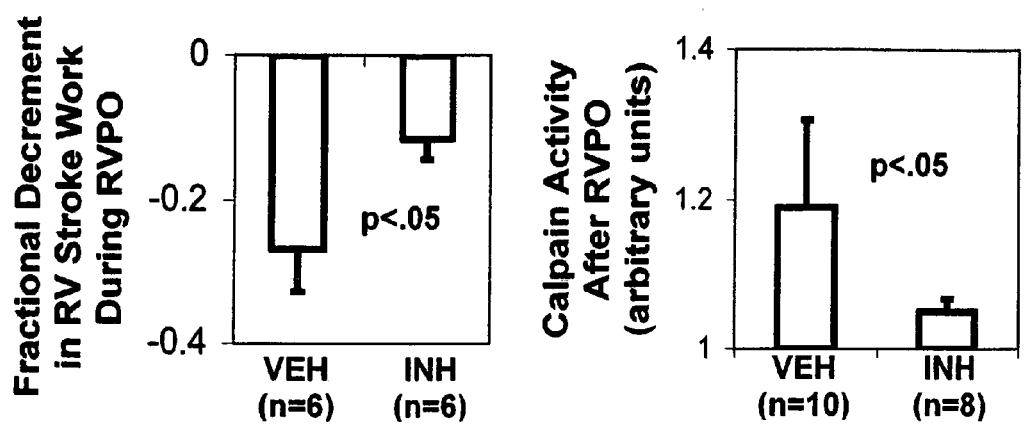

FIG. 1 illustrates the effects of the cysteine protease inhibitor MDL-28170 on RV function and spectrin degradation during four hours of sustained RV pressure overload. Anesthetized open chest pigs were randomized to treatment with MDL-28170 (INH) or inactive vehicle (VEH) infused into the right coronary artery, then subjected to RV pressure overload by a constant degree of pulmonary artery constriction for 4 hrs. Contractile function was assessed by global RV stroke work. In a second series of experiments, calpain activation after RV pressure overload was assessed by Western blotting of spectrin breakdown products. At the beginning of RV pressure overload, RV systolic pressure was 60±5 mmHg in both groups. Compared with vehicle-treated pigs, MDL-28170 treated pigs maintained significantly higher RV stroke work during 4 hrs RV pressure overload (Figure Left). RV myocardium from MDL-28170 treated pigs showed less calpain activation after RV pressure overload than vehicle treated pigs (Figure Right). Four vehicle treated pigs, but no MDL-28170 treated pigs, failed to complete the protocol due to RV failure and hypotension and were not included in this analysis. Thus, RV dysfunction during RV pressure overload is attenuated by cysteine protease inhibition, offering a potential new therapeutic strategy in this condition.

Example 2

Experimental Studies of RV Dysfunction

It has been demonstrated that RV dysfunction persists following a brief period of RV pressure overload despite restoration of normal loading conditions (39). Such persistent dysfunction is analogous to the "stunning" that occurs in the LV following restoration of blood flow after ischemia. In an initial description of this phenomenon, chloralose-anesthetized, autonomically blocked, open-chest pigs were subjected to pulmonary artery constriction causing RV pressure overload (increase of peak RV systolic pressure to 55±1 mmHg from a baseline of 35±1 mmHg). After one hour of pressure overload, pulmonary artery constriction was released, and RV contractile function assessed one hour later. The resulting RV dysfunction is demonstrated in FIG. 2A, which shows regional pressure versus segment length relations in the RV free wall of a pig under baseline conditions (black lines) and one hour after restoration of baseline loading conditions (gray lines) following an hour of pressure overload. Bold loops A (baseline) and A' (post-pressure overload) were obtained under steady-state conditions before inferior vena cava occlusion. Note that gray loop A' (post-pressure overload) has greater end-diastolic segment length and nearly identical end-diastolic pressure compared with black loop A (baseline), but loop area (i.e., external work) and RV free wall fractional shortening are lower at one hour after relief of pressure overload compared with baseline.

FIG. 2B shows regional Frank-Starling relations derived from the data in FIG. 2A. The use of the regional Frank-Starling relation to assess regional contractility is described in detail herein. The rightward and downward shift in the regional Frank-Starling relation from baseline (black line) to one hour after restoration of baseline loading conditions (gray line) indicates that a reduction in regional contractile function occurred in the RV free wall following acute pressure overload, because less regional external work is performed at any given level of regional preload.

In a recent investigation of RV dysfunction, both a reduction in slope and a rightward shift in the regional Frank-Starling relation together contributed to the decrease in preload-adjusted regional external work following acute RV pressure overload (40). The physiologically important consequence of either a decreased slope or increased intercept in the regional Frank-Starling relation is a reduction in work at a given set of loading conditions. The practical, clinically relevant consequence is that the RV must be distended to a greater volume to generate the same amount of stroke work, resulting in impaired cardiac performance since RV dilation negatively affects LV output in closed-chest patients.

Autonomic blockade was used to prevent compensatory reflexes because intrinsic dysfunction might otherwise have been masked by increased sympathetic tone. Moreover, reflex alterations in heart rate and sympathetic tone over the course of the experiment and during vena cava occlusions (which are used to generate the range of loading conditions required for assessment of contractility) interfere with interpretation of regional Frank-Starling relation.(41) Therefore, the possibility that autonomic blockade or anesthetics used during the experiment could themselves have contributed to progressive RV contractile dysfunction was investigated. Sham-operated pigs treated identically to pressure-overloaded pigs were monitored for 3 hours without RV pressure overload; no change in RV contractility as assessed by the regional Frank-Starling relation over the duration of the experiment was found indicating that autonomic blockade, anesthesia and surgical instrumentation themselves do not result in progressive RV dysfunction. The possibility that humoral factors released consequent to prolonged RV pressure overload could have contributed to generalized myocardial depression, which would have affected both the RV and the LV was investigated. Pigs instrumented with sonomicrometry crystals and micromanometer-tipped catheters in both the LV and RV were again subjected to one hour of RV pressure overload followed by one hour of recovery. In those pigs, severe RV systolic dysfunction occurred in the recovery period without any significant changes in LV function. Thus, RV dysfunction following pressure overload is not due to circulating depressant factors.(42)

Example 3

Figure 3:
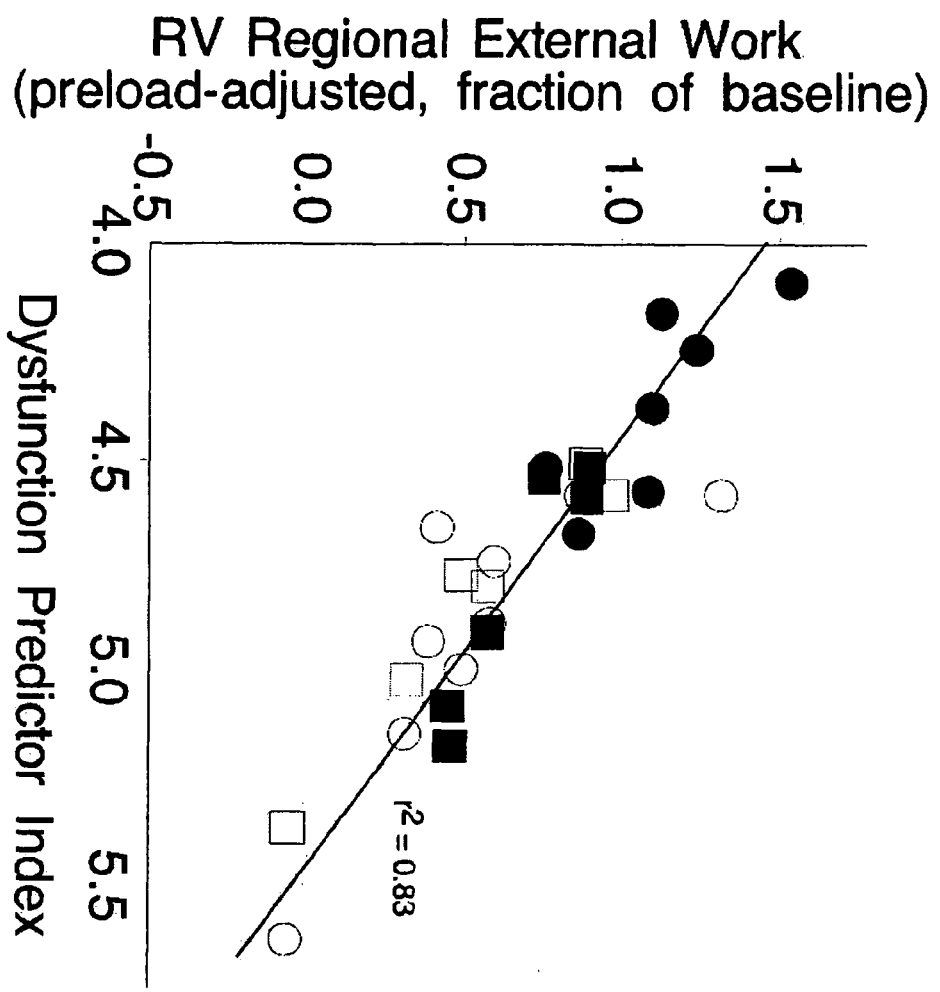

In subsequent studies, it was found that the severity of RV dysfunction following relief of RV pressure overload was directly related to the severity of RV free wall stress during pressure overload.(43) Chloralose-anesthetized, autonomically blocked open-chest pigs were again subjected to one hour of RV pressure overload caused by pulmonary artery constriction, followed by one hour of recovery after release of pulmonary artery constriction. A wide range of RV free wall systolic stress during RV pressure overload was achieved by either closing or opening the pericardium (to prevent or allow RV dilatation), and by administering or not administering dobutamine (to alter RV systolic pressure). LV pressure was maintained at a constant level with phenylephrine. FIG. 3 shows the strong relation between regional RV free wall dysfunction one hour following RV pressure overload and the dysfunction predictor index, a surrogate for RV free wall stress calculated from the values of two hemodynamic variables during RV pressure overload: RV dimensions at peak RV systolic pressure (determined by sonomicrometry) and peak RV systolic pressure.

Example 4

Experiments were undertaken to determine if ultrastructural alterations typical of cytoskeletal disruption occur in RV myocardium subjected to acute pressure overload. In one exemplary method, Pigs (n=9) were subjected to one hour of pulmonary artery constriction to cause RV pressure overload (peak RV systolic pressure 65 mmHg vs. 35 mmHg at baseline) as described in the methods, or instrumented identically but not subjected to pulmonary artery constriction. Hemodynamic measurements were repeated one hour after release of pulmonary artery constriction, or at the corresponding time in control pigs. Preload-adjusted regional external work, a loading condition-independent index of regional contractile function derived from the regional Frank-Starling relation, was determined in the RV free wall as previously described in (47). At the conclusion of the experiment, hearts were arrested in diastole and perfusion-fixed with glutaraldehyde-paraformaldehyde at zero distending pressure. Transmission electron microscopy was performed on specimens from the RV free wall, and 200-300 sarcomeres from each heart were measured.

Figure 5A:
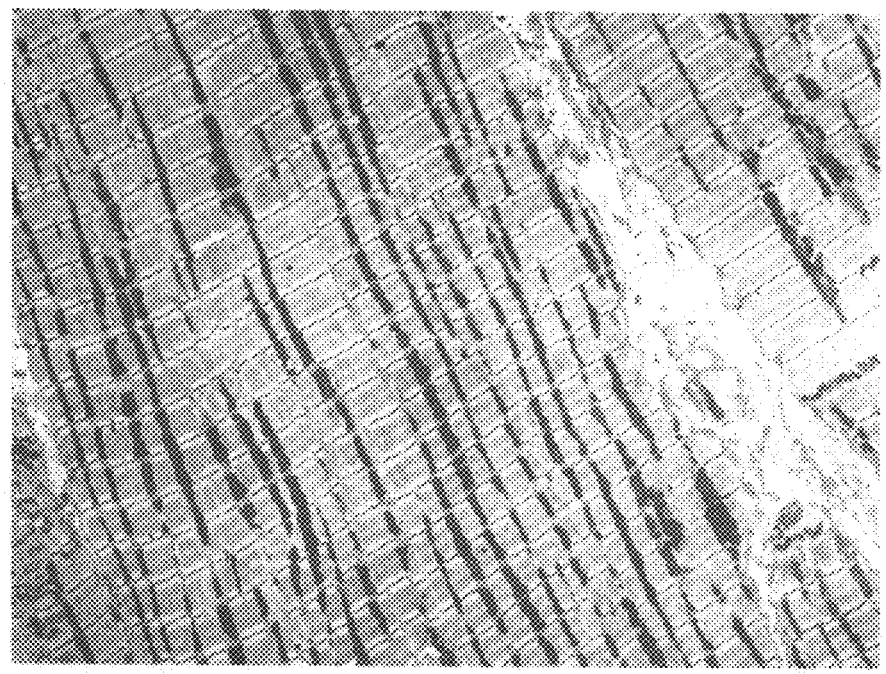
FIGS. 5A and 5B illustrate a representative electron micrograph of RV myocardium from a pig subjected to 1 hr of acute RV pressure overload (RV systolic pressure 60 mmHg, FIG. 5B) and from a control pig not subjected to acute RV pressure overload (FIG. 5A).
Figure 5B:
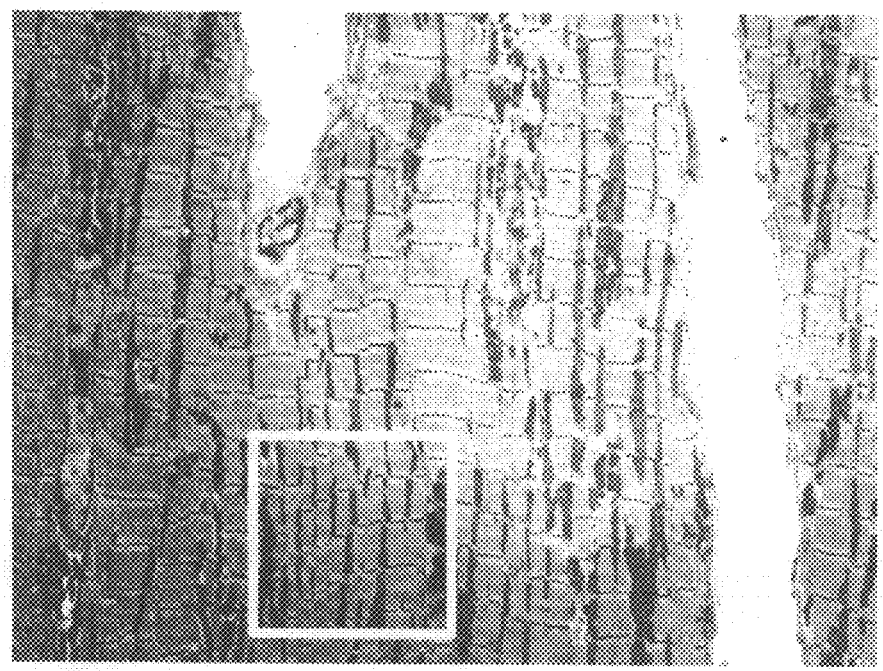

In one example, pigs subjected to RV pressure overload exhibited severe RV regional dysfunction after release of pulmonary artery constriction, versus no change from baseline in control pigs. FIG. 5A shows a representative transmission electron micrograph from a control pig. Note in the control there are regular arrangements of sarcomeres and a consistent Z-line registration across the field. FIG. 5B shows a representative transmission electron micrograph from a pressure overload pig. Here, disorganized and misaligned Z-lines are shown. There was no evidence of disruption of mitochondrial cristae, suggesting that ischemic injury did not occur in these pigs. Nevertheless, despite disruption of the regular sarcomeric Z-line arrangement, there was no difference in mean sarcomere length between the pressure overload hearts (1.83±0.15 µm) and control hearts (1.82±0.19 µm). FIGS. 5A and 5B. Electron micrographs of RV myocardium from a pig subjected to 1 hr of acute RV pressure overload (RV systolic pressure 60 mmHg, FIG. 5B) and from a control pig not subjected to acute RV pressure overload (FIG. 5A) are shown. Here, the orderly sarcomere Z-line structure in the control pig in FIG. 5A; in contrast with the irregular, misaligned Z-line structure in the pressure-overloaded pig in FIG. 5B, suggests degradation of cytoskeletal proteins may be responsible for maintaining sarcomere architecture. However, there was no significant difference in mean sarcomere length between control and pressure overload myocardium.

Since disruption of the sarcomeric Z-line may be caused by degradation of the cytoskeletal proteins desmin or α-actinin, these results indicate the degradation of cytoskeletal proteins may cause sarcomeric disorganization and contributes to RV dysfunction following pressure overload.

Example 5

RV Pressure Overload and Protein Concentration

Fluorescent two-dimensional difference gel electrophoresis image with RV pressure overload myocardium stained with Cy3 and sham myocardium stained with Cy5. Arrow numbers 2 and 4 indicate increased protein levels, while arrow numbers 1 and 3 indicate decreased protein levels. Proteins with altered levels may be identified using tryptic digestion and MALDI/TOF mass spectrometry in combination with peptide fingerprinting software. See methods for detailed description of two-dimensional difference gel electrophoresis.

Example 6

Are Myofibrillar or Cytoskeletal Proteins Altered in Porcine RV Myocardium Following Acute Pressure Overload In one exemplary method, experiments were undertaken to determine whether RV dysfunction after acute pressure overload is associated with alterations in myofibrillar regulatory or cytoskeletal proteins. Transmural drill biopsies of the RV free wall were obtained from control pigs and from pigs subjected to acute RV pressure overload, freeze-clamped in liquid nitrogen within 10 s of the biopsy, and subjected to two-dimensional SDS polyacrylamide gel electrophoresis (2D-PAGE) and Western blotting as described in the Methods. Protein spots were excised, subjected to in-gel tryptic digestion, and analyzed using MALDI-TOF mass spectrometry. The figures show gels from a control pig (FIGS. 7A and 7B) and from a pig subjected to 15 min RV pressure overload (FIG. 8), and their corresponding Western blots after probing with polyclonal anti-desmin antibody. Mass spectrometry of the protein spot identified as Des confirmed its identity as pig desmin (spectrum shown in FIG. 9). Comparing FIG. 8 with FIGS. 7A and 7B, note the change in appearance of the constellation of spots designated Des and Des-Phos, and the appearance of several new spots in the RV pressure overload pig (FIG. 8) recognized by anti-desmin antibody, designated Des-Deg and 40-50 kDa. A similar pattern has been reported following incubation of desmin with calpain in vitro (48). The spots designated Unk, a 40-50 kDa protein have not yet been identified. The spots designated Des-Deg and Unk are relatively low abundance (as indicated by the absence of Coomassie staining on the corresponding PAGE gels), but were nevertheless consistently present in myocardium from all 6 pigs subjected to RV pressure overload analyzed to date. These data indicate that desmin degradation occurred as a consequence of RV pressure overload.

FIGS. 7A and 7B. Coomassie-stained 2-D PAGE gel of right ventricular myocardium (FIG. 7A) and its corresponding Western blot (obtained by direct transfer to a PVDF membrane) probed with polyclonal anti-desmin antibody (FIG. 7B) from a control pig. The spot marked Des in the left panel was identified as pig desmin by MALDI-TOF mass spectrometry. The spots marked Des-Phos in FIG. 7B are likely phosphorylated forms of desmin based on their acid shift.

FIG. 8. Coomassie-stained 2-D PAGE gel of right ventricular myocardium (left panel) and its corresponding Western blot probed with polyclonal anti-desmin antibody (right panel) from a pig subjected to 15 min acute right ventricular pressure overload. The spots marked Des-Phos have increased in abundance compared with the spots marked Des-Phos in the control pig (FIGS. 7A and 7B), suggesting a shift from non-phosphorylated to phosphorylated desmin. The spots marked Des-Deg likely represent desmin degradation products. The identities of the spots marked Unk have not yet been determined.

The spots designated Des-Phos likely represent phosphorylated desmin based on their acid shift on 2-D PAGE and similarity to a pattern previously identified in patients with desmin myopathy (Caron, et al., 1999). The relative increase in this presumed phosphorylated fraction of desmin in the RV pressure overload pig (FIG. 8) is consistent with a shift from an insoluble cytoskeletal fraction (unphosphorylated) to a soluble cytosolic fraction (phosphorylated). The spots designated Des-Deg in FIG. 8 likely represent proteolytic fragments of desmin.

It has also been demonstrated that severe RV dysfunction and desmin degradation occur in pigs subjected to acute RV pressure overload even in the absence of pharmacological autonomic blockade. Four pigs were subjected to 90 min of RV pressure overload (60 mmHg RV systolic pressure compared with 32 mmHg at baseline) without pharmacological blockade (i.e., no atropine or propranolol). Desmin content in myocardial biopsies obtained at baseline and following RV pressure overload was determined in two of the pigs using 2D PAGE as described in the Methods; the content in the main desmin spot was normalized to total spot density in each gel. Table 2 shows the results. In summary, preload-adjusted regional external work 30 min following release of pulmonary artery constriction was reduced from baseline (in all four pigs) by an average of 36% ($p<0.05$). The severity of dysfunction was somewhat less than previously observed in pharmacologically blocked pigs subjected to pressure overload, likely because intrinsic contractile dysfunction was partially masked by compensatory reflexes causing adrenergic stimulation. Desmin content in the main spot was reduced from baseline in both pigs analyzed by an average of 21%.

It may be possible to identify other proteases contributing to cytoskeletal protein degradation by analysis of cytoskeletal degradation patterns using 2D electrophoresis and mass spectrometry, thus providing other potential targets for inhibition.

Example 7

Are Matrix Metalloproteinases Activated by Acute RV Pressure Overload

In one exemplary method, experiments were performed to determine whether acute RV pressure overload causes activation of MMPs. Six pigs were subjected to 90 min acute RV pressure overload followed by 30 min recovery; 5 identically instrumented pigs underwent sham pressure overload over the same time period. Specimens of RV myocardium were obtained from the area subtended by the sonomicrometry crystals at the end of the experiment, and analyzed for MMPs and their tissue inhibitors (TIMPs) as described in the Methods. Pigs subjected to acute pressure overload manifested severe dysfunction as observed in prior investigations, with no dysfunction detected in the sham controls. Latent and active MMP-2 (gelatinase A), and latent MMP-9 (gelatinase B) increased with RVPO (Table 3). TIMP-1 and TIMP-3 decreased by 58% and 34% respectively, but there were no significant differences in TIMP-2

The technique employed to determine active and latent collagenase activity (digestion of tritiated Type I collagen by tissue extract) detects total tissue collagenase activity, including contributions from MMP-1, MMP-2, MMP-8, MMP-9 and MMP-13; since any digestion of tritiated Type I collagen in whole-tissue extract was not detected, it is unlikely that any significant collagenase activity was present in these tissue specimens. Moreover, even if qualitative evidence of ECM degradation is not found, it is still possible that degradation of other cellular components by MMP-2, such as basement membrane or cardiac troponin could contribute to the development of contractile dysfunction in this model. As discussed previously, proteomics-based investigation can identify alterations in proteins not initially targeted for investigation. Such an approach, in combination with the use of an MMP-2 inhibitor, may help elucidate whether MMP-2 activation contributes to the development of acute RV contractile dysfunction acutely following pressure overload.

Example 8

Does the Response to RV Pressure Overload Vary Regionally Across the RV Free Wall Single pairs of crystals to measure segment length demonstrate no difference in the regional Frank-Starling relation in the RV inflow and outflow tracts. However, since the severity of RV contractile dysfunction correlates with regional RV systolic stress, it regional heterogeneity of shape would likely result in regional heterogeneity of wall stress and hence in regional heterogeneity of the resulting contractile dysfunction. In one exemplary method, experiments in which two square arrays of 4 crystals each were implanted in the central anterior RV free wall and approximately 6 centimeters away in the apical RV free wall of the pigs were performed. A multichannel digital sonomicrometer was used to determine the instantaneous separation of all potential pairs of crystals, and standard equations used to calculate the area subtended by the crystals and the angles between orthogonal pairs. The angle, which ranged from 83-88 degrees, was not significantly different between control conditions and following 90 min of acute RV pressure overload in any of the pigs assessed, suggesting that any errors in the functional assessment from assuming constant orthogonality between crystal pairs in previous investigations were likely to be small.

FIG. 9. represents a spectrum obtained using MALDI-TOF on the trypsin digest of the protein spot identified as Des in FIGS. 7 and 8. After identifying the monoisotopic peaks, the peptide molecular weights were entered into MS-FIT (http://prospector.ucsf.edu), with the following options selected: peptide mass tolerance 50 ppm; minimum 4 peptides to match; identity mode; cysteines modified by carbamidomethylation; possible phosphorylation of S, T, and Y; full pI range (3-10) and molecular weight range (1000-100,000 Da). The 27 peptide peaks identified and matched using MS-FIT comprised more than 50% of the amino acids in the desmin sequence, resulting in a MOWSE score of $5 \times 10^{12}$, an extraordinarily high-probability match. The predicted pI and MW were exactly the same as the calculated pI and MW of the protein spot on the gel. Other porcine myocardial proteins definitively identified using these techniques so far include tropomyosin, myoglobin, myosin light chain 1, cardiac a-actin, alpha-B-crystallin, muscle-type aldolase, isocitrate dehydrogenase, and malate dehydrogenase.

FIG. 11. Western Blot of Myosin

One potential mechanism of RV dysfunction in acute RV pressure overload is impaired myosin function from stress-induced myosin.(67) FIG. 11 shows a Western immunoblot (anti-myosin antibody clone MF-20, Iowa Hybridoma Bank) of myocardial tissue homogenate from open chest pigs subjected to acute RV pressure overload manifesting dysfunctional myocardium (lane numbers 4, 5, 8, 9, 10) compared with sham operated pigs not subjected to pressure overload with normal contractile function (lane numbers 1, 2, 3, 6, 7, 11, 12). The total myosin signal is increased in dysfunctional RV myocardium. Lanes 13 and 14 are from tissue digested in vitro with calpain. The reason for increased myosin signal in the dysfunctional myocardium may indicate an increase in myosin solubility similar to one study where myosin glycosylation increases myosin solubility in low-ionic strength buffer. (68) Thus, the increased myosin signal in dysfunctional myocardium could be due to increased myosin solubility in the low-detergent, low-ionic strength homogenization buffer used secondary to myosin glycosylation. The increase in myosin signal was inhibited by MDL-28170. The mechanism by which MDL-28170 could inhibit stress-induced myosin glycosylation is unknown, but alterations in calpain-like proteases can alter sensitivity to glycosylation in some model systems. (68)

Protocols

Statistical Methods.

Alterations in RV contractile function are reported as mean±standard error of measurement, and compared using t-tests and the Bonferroni correction for multiple comparisons. Where significant differences are identified, the relationship between alterations in protein content, myofibrillar ATPase activity, and severity of RV contractile dysfunction are tested using linear regression, with the correlation coefficient tested for significance.

Proteomics Techniques

Two-Dimensional Polyacrylamide Gel Electrophoresis.

RV biopsies are homogenized on ice in 10 vol Buffer I (50 mM Tris pH 8.0, 0.2 M DTT, 0.3% SDS, 1 mM AEBSF (4-(2-aminoethyl) benzenesulfonyl fluoride), 0.1 mM leupeptin, 10 µg/ml aprotinin). Next, 1/10 volume Buffer II (0.5 M Tris, pH 8.0, 50 mM $MgCl_2$, 2000 units/ml DNAase I, 750 units/ml RNAase A) is added and the specimen allowed to incubate for 10 min on ice. The proteins are then quantitatively precipitated with methanol/chloroform (49). After drying, the pellets are resuspended in isoelectric focusing buffer containing urea, thiourea, CHAPS, DTT, and ampholytes (IPG Strip Rehydration Buffer from Genomic Solutions, Inc. or equivalent, supplemented with 2M thiourea and 50 mM DTT), and allowed to stand overnight. Unsuspended material is pelleted, the supernatant assayed for protein content (Bradford method), and then diluted with additional IPG buffer to a final protein concentration of 2.5 mg/ml. Immobilized pH gradient (IPG) strips (Pharmacia or equivalent) are rehydrated overnight with 400 µl of the resulting IPG buffer (1.0 mg total protein), and the strips focused for 24 hrs to a total of 100,000 Vh. Following isoelectric focusing, the second dimension is run on double-sided precast 10% SDS polyacrylamide gels after equilibrating the strips in 6 M urea, 2% DTT, 30% glycerol, 0.01% bromphenol blue, and then 6 M urea, 2.5% iodoacetamide, 30% glycerol, 0.01% bromphenol blue, for 10 min each, for reduction and alkylation of the proteins.

Protein Quantitation by 2D-PAGE.

The two-dimensional SDS polyacrylamide gels are stained with colloidal Coomassie Blue, scanned on a flatbed scanner, and analyzed using the Phoretix 5.1 gel analysis package. Molecular weights and pIs of individual protein spots are calibrated using standard molecular weight markers run on the edge of the gel, and the predicted pIs of previously identified proteins spanning the area of interest. Protein content is standardized to total integrated intensity of all identified spots and normalized to baseline. Alternatively, fluorescence two-dimensional differential gel electrophoresis may be helpful (50). This technique is identical to that described above with the exception that protein extracts from two different experiments that are to be compared are covalently stained with different fluorescent "Cy-dyes" before electrophoresis and run concurrently on the same 2D-PAGE gel. Using a multi-color imager, the two samples can then be imaged simultaneously on the same gel, permitting perfect superposition of protein spots and facilitating quantitative comparisons.

Statistical Analysis. Changes in protein abundance or phosphorylation state (i.e., a change in spot intensity of a phosphorylated protein, identified from an acidic shift on 2D-PAGE) are considered significant when the integrated spot intensity of matched spots in paired baseline and recovery biopsies are consistently increased or decreased. Briefly, pairs of gels from baseline and recovery biopsies in each pig are matched and differences in abundance calculated for each matched spot. Paired gels are normalized as described. Once all gels are matched, the Wilcoxon nonparametric paired t-test is used to determine which spots consistently change from baseline to recovery. Spots that are consistently changed in pressure overload but not in control pigs are considered significant candidate proteins, and are identified using mass spectrometry/peptide fingerprinting.

Protein Identification by Mass Spectrometry.

Spots of interest are excised from the gel, washed (50% acetonitrile/25 mM ammonium bicarbonate followed by 100% acetonitrile), dried, rehydrated on ice for 20 min in 20 µl porcine trypsin for in-gel digestion (20 µg/ml in 10% ammonium bicarbonate), then incubated overnight at 37° C. The gel pieces are then extracted with 50% acetonitrile/5% trifluoroacetic acid, and the eluants concentrated using Millipore Zip Tips. MALDI-TOF mass spectrometry is performed using a Perseptive Systems Voyager DE system after spotting protein eluants onto MALDI-TOF plates with matrix (α-cyano-4-hydroxycinnamic acid). The instrument is calibrated with a known peptide standard (des-arg$^1$ bradykinin/angiotensin I/glu$^1$-fibrino-peptide B/ACTH$_{18-39}$). Proteins are identified from the resulting spectra using peptide fingerprinting with the MS-FIT database search program (http://prospector.ucsf.edu). Altered phosphorylation of proteins is confirmed by observing 80 Da shifts (corresponding to phosphate groups) in peptide fragments. Protein degradation products are also identified using this technique, with their coverage maps, pI and molecular weight suggesting possible cleavage sites.

Experimental Protocols

Research Design and Methods

Animal care: Domestic farm pigs (25-40 kg) are sedated with IM injection of ketamine HCl, followed by IV administration of fentanyl or propofol and α-chloralose. In most exemplary protocols, experiments are performed under deep general anesthesia using α-chloralose. Following anesthetic induction, pigs are intubated via tracheotomy and ventilated using a pressure-cycled ventilator. Mechanical respiration is adjusted to maintain physiologic values of arterial pH, pO2, and pCO$_2$. All experiments are non-survival: at the conclusion of each experiment, supplemental α-chloralose is given prior to inducing ventricular fibrillation (KCl 10%, 25 cc infused IV). Myocardial tissue is harvested immediately for histologic and/or biochemical analysis.

Instrumentation and Hemodynamic Measurements. The experimental preparation is similar to that previously described (51). After exposure via median sternotomy, the heart is instrumented as illustrated in Appendix A.

Pigs are autonomically blocked using propranolol (1 mg/kg every 3 hours) and atropine (0.2 mg/kg). For calpain inhibitor experiments, the proximal portion of the right coronary artery is dissected free, fitted with a transit-time ultrasonic flow probe, and cannulated with a 26 g polyethylene catheter as described (52). Digitized hemodynamic data are analyzed as previously described (53) and in Appendix A.

RV Biopsies. 50 mg biopsies of the RV free wall (4 mm diameter) are obtained under baseline conditions and after varying time periods using a high-speed drill as previously described (Greyson, et al., 1995). Specimens are freeze-clamped on a liquid-nitrogen cooled mortar within 15 s of collection, then stored under liquid nitrogen for SDS-PAGE, or at −80° C. for calpain activity assays. Paired biopsies from each pig are always handled and processed in parallel for all subsequent steps.

Protein quantitation by Western blotting (see Tables 4 and 5 for proteins considered likely to be degraded during RV pressure overload and contributing to RV contractile dysfunction). All steps are performed at 4° C. Briefly, tissue is homogenized in 10 vol of buffer (20 mM PIPES, pH 7.6, 1 mM EDTA, 1 mM DTT, 50 µg/ml leupeptin, and 10 µg/ml each of AEBSF and aprotinin). Bradford protein assay is performed. 4-12% bis-tris gradient mini gels are run using MES buffer. Proteins are transferred to PVDF membranes using Towbin transfer buffer. Membranes are blocked in 5% nonfat milk in Tris buffered saline (20 mM Tris-HCl, 0.15 M NaCl, TBS) for 2 hrs at RT, incubated with primary antibody diluted in Tris-Tween buffer (TBS plus 0.1% Tween-20, TTB) for 2 hrs at RT, and rinsed 3 times for 10 min in TTB. Membranes are then incubated in HRP-conjugated secondary antibody diluted in TTB for 1 hr at RT, rinsed 4 times in TTB for 10 min each, then visualized on x-ray film using an enhanced chemiluminescence kit. Several antibodies to epitopes spanning each protein, or polyclonal antibodies raised to native protein, will be chosen to permit identification of protein degradation products. Quantitation is performed using standard methodology by scanning and densitometric analysis.

Calpain and caspase activity. Most assays of calpain activity measure total calpain activity of tissue homogenates, rather than the fraction of total calpain that has been activated in vivo. Therefore, rather than determining total calpain activity of tissue homogenates, calpain activity of baseline and post-pressure overload RV biopsies are determined by assaying the presence of spectrin breakdown products (SBPs). The procedure is identical to that described for protein identification and quantitation by Western blotting, above, with the use of anti-spectrin antibodies. In vivo calpain activity is then determined as the integrated intensity of the SBP band normalized to the integrated intensity of the spectrin band. Both calpain and caspase may degrade spectrin. To distinguish spectrin degradation by calpain from spectrin degradation by caspase, calpain-specific degradation bands (145 kD) and caspase-specific degradation bands (120 kD) are quantified separately; these bands will be definitively identified by running concurrent standards consisting of purified spectrin digested in vitro by calpain and caspase, respectively.

Matrix metalloproteinase content and activity. At the conclusion of the experiment, transmural samples from the RV free wall weighing 100-200 mg are rapidly excised and frozen in liquid nitrogen. Samples are analyzed for MMPs and tissue inhibitor (TIMP) activity (54). Briefly, samples are homogenized and extracted sequentially in extraction buffer (0.25% Triton X-100/50 mM Tris-HCl, pH 7.5), and 1 M guanidine/ extraction buffer, and the combined extracts dialyzed against standard Tris buffer. All steps are carried out at 4° C.

Gelatin zymography is performed to determine tissue content of MMP-2 and MMP-9. Briefly, SDS-PAGE is performed in 7.5% or 10% polyacrylamide containing 0.33 mg/ml gelatin, and the gels incubated for 18 h at 37° C. in assay buffer. Gels are stained with Coomassie blue R-250, scanned, and analyzed using NIH Image to generate peaks for the lanes on the gel corresponding to latent and active forms of each MMP. To calculate myocardial enzyme content in units of ng enzyme per gram wet weight tissue, experimental peaks are calibrated from peaks obtained with MMP standards added to each zymogram gel and bracketing a linear range of assay. TIMPs are semi-quantitated using SDS-PAGE and Western blotting with specific antibodies.

Ultrastructural Analysis. Perfusion fixation and transmission electron microscopy of the RV is performed as previously described for the LV (Lu, et al. 2001). In each pig, 10 fields randomly selected from each of 5 blocks obtained from the RV endocardium and 5 blocks obtained from the RV epicardium are photographed at a magnification of ×5000. There is currently no established method for quantitative analysis of sarcomere Z-line organization. Therefore, a single observer blinded to the experimental intervention will qualitatively score the Z-line organization in each photograph on a 1-4 scale: 1) regular, ordered structure; 2) mildly disrupted; 3) moderately disrupted; 4) severely disrupted. Scores for the 100 photographs from each pig will be averaged to obtain a summary score ranging from 1 to 4.

Collagen ultrastructure will be assessed using the cell maceration scanning electron microscopy technique. This technique allows removal of cellular elements while leaving the collagen architecture of the myocardium intact and accessible for imaging by scanning electron microscopy, and has been described in detail previously. Briefly, hearts are perfusion-fixed in situ using cold neutral buffered formalin; 3-mm cubes of fixed tissue are immersed in 10% NaOH for 3 days at room temperature, rinsed in distilled water for 1 or 2 days, treated with 1% aqueous tannic acid for 2-3 h, and rinsed in distilled water for several hours. They are postfixed in a 1% aqueous solution of osmium tetroxide for 1-2 h, dehydrated in graded alcohols according to standard methods, frozen in liquid nitrogen and cracked with a cooled razor blade; the resulting pieces are placed in acetone before being transferred to tetramethylsilane for 10 min. Subsequently, the tissue is air dried at room temperature, sputter-coated with gold-palladium, and examined in a scanning electron microscope. Electron micrographs were analyzed qualitatively by a reader blinded to the experimental condition of the pig from which the tissue was taken.

Calpain has been reported to participate in activation of caspase-mediated apoptotic pathways (55), and caspase may cleave spectrin. It is possible to concurrently assess caspase and calpain activity by identification of specific spectrin breakdown products. Tensin and focal adhesion kinase may be protein targets that play a role in the mechanism of RV contractile dysfunction. Another target may be integrin-mediated signaling in chronic RV pressure overload.

Adrenergic signal transduction may play a role in the initiation of the signaling cascade that culminates in RV contractile dysfunction. While it is unlikely that beta-adrenergic signaling plays a significant role in the development of RV dysfunction observed, since pigs subjected to RV pressure overload developed regional RV contractile dysfunction whether or not they were blocked with high doses of propranolol, a role for alterations in alpha-adrenergic signaling in the development of contractile function has not been excluded The basic experimental protocol (illustrated in FIG. 10) is an example of one possible experiment. Following baseline measurements, the pulmonary artery occluder is gradually constricted to produce the highest RV pressure obtainable without producing progressive systemic hypotension. Control pigs undergo identical instrumentation, but are not subjected to pulmonary artery constriction during the experiment. Hemodynamic measurements are determined at baseline, during acute pressure overload from pulmonary artery constriction, and at the end of the experiment. Measurements of contractile function are determined at baseline and at the end of the experiment. Drill biopsies are obtained from the RV under baseline conditions and at one or two subsequent time points during the experiment. At the conclusion of each experiment, euthanasia is performed with supplemental IV anesthesia followed by IV injection of 10% KCl. Immediately after euthanasia, myocardial tissue is harvested for myofibrillar ATPase assays and electrophoretic analysis, or the heart is perfusion-fixed for structural analysis.

FIG. 10. Illustration of the experimental protocol. In all experiments to date, the total time elapsing from initial instrumentation and biopsy to final biopsy and hemodynamic measurements was kept constant to eliminate potential changes due solely to surgical and anesthetic stress. In some future protocols, the duration of PA constriction will be varied and hemodynamic measurements and biopsies obtained immediately after release of PA constriction. An additional RV biopsy may be obtained at an intermediate point during the protocol to facilitate definition of the temporal sequence of alterations in protein content, degradation and/or phosphorylation, myofibrillar ATPase activity, or alterations in calpain or MMP activity.

Protocol #1 Cysteine Protease Inhibitor Experiments

The purpose of this experiment is to determine whether calpain activation is mechanistically related to the development of RV dysfunction from pressure overload. Open-chest pigs will be instrumented as described. A 26 g polyethylene catheter will be inserted into the right coronary artery. Pigs will be either pretreated (intervention, n=12) or not pretreated (control, n=12) by intracoronary infusion of a membrane-permeable calpain inhibitor (e.g., MDL-28170 or calpain inhibitor 1). MDL-28170 will be dissolved in DMSO/phosphate buffered saline, and the rate of infusion adjusted using a coronary flow probe to achieve a final right coronary arterial concentration of 1 μM per liter MDL-28170 ($K_i$ for calpain=8 nM) and 0.1% DMSO. The infusion will be begun 30 min prior to beginning pulmonary artery constriction and continued throughout the experiment. Biopsies of the RV myocardium will be obtained, followed by baseline hemodynamic measurements. Pigs will then be subjected to RV pressure overload by constriction of the main pulmonary artery for 90 min. Hemodynamic measurements will be repeated 30 min after relief of pressure overload, and a second set of RV biopsies obtained. Tissue will be analyzed for calpain and caspase activity, MMP activity, ATPase activity (maximal calcium-activated myofibrillar ATPase activity, $pCa_{50}$ and Hill coefficients), modifications of proteins (such as degradation or phosphorylation) listed in Tables 4 and 5, and general proteomics analyses.

Protocol #2: MMP Inhibitor Experiments

The purpose of this experiment is to determine whether MMP activation is mechanistically related to the development of RV dysfunction from pressure overload. Open-chest pigs will be instrumented as described. Pigs will be either pretreated (intervention, n=11) or not pretreated (control, n=11) by oral administration of the MMP inhibitor COL-3 (an orally-active MMP inhibitor that has been shown to prevent MMP-mediated lung injury in an acute pig model) the evening before the experiment (56). Biopsies of the RV myocardium will be obtained, followed by baseline hemodynamic measurements. Pigs will then be subjected to RV pressure overload by constriction of the main pulmonary artery for 90 min. Hemodynamic measurements will be repeated 30 min after relief of pressure overload, and a second set of RV biopsies obtained. Tissue will be analyzed as described in Protocol #1.

Protocol #3: Temporal Development of RV Dysfunction.

To determine the temporal and quantitative relationship of protein alterations to the severity of contractile dysfunction, pigs will be subjected to varying durations of RV pressure overload. RV biopsies and hemodynamic measurements will be obtained under baseline conditions. Pigs (n=20) will be subjected to pulmonary artery constriction for between 15 and 90 min (i.e., 5 pigs each for 5, 15, 30, and 60 min). Immediately after release of pulmonary artery constriction a second set of hemodynamic measurements will be obtained, immediately followed by a second RV biopsy. Biopsies obtained under baseline conditions and at the end of the experiment will be analyzed for protein content, phosphorylation state and/or degradation products as described. Western blots from 2D-PAGE gels will be probed with monoclonal antibodies to the proteins listed in Table 4, while Western blots from 1 D-PAGE gels will be probed with monoclonal antibodies to the proteins listed in Tables 4 and 5. Degradation products will be identified as spots staining with specific antibodies at smaller molecular weights than the parent proteins. Altered phosphorylation state will be identified by the acidic shift from the parent proteins on 2D-PAGE gels. The identity of proteins that change significantly in pressure-overload pigs, but not in control pigs (with $p<0.05$ not corrected for multiple comparisons), will be confirmed using MALDI-TOF, with potential cleavage or phosphorylation sites suggested by alterations in the mass peptide profiles as described in the methods. RV myocardium will also be analyzed for calpain activity or for content and activity of MMPs as described in the methods. Data from this series of experiments will be combined with data obtained from Protocols #1, #2 and #4 for statistical analysis.

Protocol #4: Sustained RV Pressure Overload

The purpose of this experiment is to determine whether inhibition of calpain activation attenuates progressive global RV dysfunction during sustained acute pressure overload. Pigs will be instrumented and treated as described above. Control pigs and inhibitor pigs will be treated with intracoronary administration of the vehicle or MDL-28170, respectively. After baseline hemodynamic measurements, the pulmonary artery constrictor will be adjusted to achieve the highest sustainable RV systolic pressure, and then fixed in place. Rather than releasing pressure overload after 90 min as in Protocols #1 and #2, pulmonary artery constriction will be maintained for a total of four hours without adjustment. RV preload (RV end-diastolic pressure) will be maintained at 8-10 mmHg by infusion of normal saline. It is not possible to reliably assess intrinsic regional RV contractile function during acute pressure overload because even so-called loading condition-independent indices of contractile function are sensitive to extremes of load. Therefore, global RV performance will be assessed using peak RV systolic pressure, RV dP/dt, and cardiac output as measured with the pulmonary flow probe; load dependent regional function will be assessed by changes in maximum principal deformation and angle, and fractional area reduction, using the sonomicrometry crystals. LV and RV free wall-septal distances will be used to determine whether changes in cardiac output are attributable to changes in septal position.

Protocol #5: Structural Alterations.

Open-chest pigs will be instrumented as described. Following baseline hemodynamic measurements, pigs will be subjected to RV pressure overload by constriction of the main pulmonary artery for 90 min; 30 min after relief of pressure overload, hemodynamic measurements will be repeated, the heart arrested with 10% KCl, and perfusion fixed with glutaraldehyde-paraformaldehyde for transmission electron microscopy (n=6) or neutral buffered formalin for cell maceration-scanning electron microscopy (n=6). Sham pigs (n=12) will be treated identically except that RV pressure will not be increased by pulmonary artery constriction.

Proteomics Analysis

The experimental protocols and methods described above are suitable for targeted investigation of specific candidate proteins suspected to be involved in the development of RV contractile dysfunction from acute pressure overload. All tissue specimens obtained during the course of this investigation will be subjected to 2D-PAGE in addition to the conventional methods of analysis described in the Methods. The 2D-PAGE gels will be analyzed using proteomics techniques as described in the Methods. Using the statistical analysis described, unknown protein spots that change consistently in concert with the development of contractile dysfunction will be identified. Those protein spots will then be subjected to in-gel tryptic digestion and peptide fingerprinting analysis by MALDI-TOF mass spectrometry as described. This analysis will permit identification of significant changes in protein abundance and post-translational modifications occurring during the development of RV contractile dysfunction not hypothesized a priori to be mechanistically related to the development of RV dysfunction.

Proteomics, or large scale protein expression profiling, which has only become possible with the development of semi-automated image analysis tools, permits simultaneous assessment of up to several thousand different proteins and their post-translational modifications at a time. Thus, a priori hypothesis testing is not the goal of this aspect of the investigation. Rather, the purpose is to generate new hypotheses for further targeted investigation. It should be noted that the finding of a change in desmin abundance following pressure overload on 2D-PAGE gels performed during an initial proteomics-based investigation led to the calpain hypothesis proposed herein.

Recent advances in two-dimensional SDS polyacrylamide gel electrophoresis (2D PAGE), mass spectrometry instrumentation, and software tools now permit rapid and reliable identification of proteins using "peptide fingerprinting". These techniques, now commonly referred to as "proteomics", may identify proteins present in 2D PAGE gels at the 100 to 500 femtomol level (57). However, identification of proteins using peptide fingerprinting is dependent on the availability of a database of candidate proteins. Most standard databases (such as Swiss-Prot and Trembl) contain a preponderance of human and mouse proteins, with relatively few porcine proteins. Nevertheless, the high degree of homology between many porcine and human or mouse proteins, and database software that permits searching for protein homologies, often permit identification of previously unindexed proteins (58). Use of antibodies specific to the proteins hypothesized a priori to be mechanistically related to RV dysfunction will help speed identification of these proteins, since polyclonal and monoclonal antibodies to human and murine proteins commonly exhibit cross-reactivity to porcine proteins. In cases where significant doubt about the identity of proteins remains, protein sequencing using mass spectrometry with post-extraction decay is possible. Using this approach it has been possible to unambiguously identify proteins from mammalian species and bacteria with poor representation in standard databases (59).

Assay of in vivo calpain activation, as opposed to total calpain activity, is dependent on identification of calpain-specific spectrin breakdown products (SBPs). The relative time course of spectrin degradation and degradation of other proteins is uncertain; however, SBPs were detectable prior to histologic evidence of tissue injury following 10 min of ischemia in rat forebrains, suggesting SBPs are early and sensitive indicators of in vivo calpain activity (60).

Although direct measurement of in vivo protease activity in the presence of inhibitors is not possible since non-covalently bound inhibitors (including endogenous TIMPS) dissociate in existing assay systems, proof of effective in vivo protease inhibition may be indirectly established by demonstrating attenuation of spectrin breakdown or of ECM alterations.

Appendix A: Instrumentation and One Method of Hemodynamic Analysis

The instrumentation of the heart is similar to what has been described previously (61). A solid-state micromanometer catheter is introduced into the RV via an internal jugular vein. A hydraulic occluder is placed around the inferior vena cava to alter preload. An ultrasonic transit-time flow probe is placed around the main pulmonary artery for measurement of cardiac output. An umbilical tape snare is placed around the main pulmonary artery to produce RV pressure overload. In addition to the instrumentation illustrated here, a Millar catheter is inserted into the left ventricle and pacing wires are affixed to the left atrium. For calpain inhibition experiments, a 26 g catheter is inserted into the proximal right coronary artery.

Orthogonal pairs of piezoelectric crystals (indicated by x in the figure) are implanted in the central anterior RV and apical RV free walls for determination of segment shortening using a sonomicrometer; the letters a-d, p and q indicate chord lengths determined using sonomicrometry used to calculate the area subtended by the crystal arrays. Two additional sonomicrometry crystals are implanted in the center of the interventricular septum through a needle track adjacent to the left anterior descending coronary artery, and in the LV free wall, for continuous assessment of LV- and RV free wall-septal distances using the digital sonomicrometer.

The instantaneous wall area, k, subtended by each square sonomicrometry crystal array is continuously calculated from the formula $$k=\sqrt{4p^2q^2-(b^2+d^2-a^2-c^2)^2}/4 \text{ where p, q, a, b, c, and d are the chord lengths}$$

between crystals as indicated, determined instantaneously by the digital sonomicrometer.

Calculation of principal deformations and deformation angles to a hemodynamic assessment was added. Principal deformations of the mid-RV free wall are determined by calculating the coordinates of the two triangular arrays of crystals defined by the four sonomicrometry crystals (i.e., the triangles defined by the chords abp and cdp in the figure), relative to the axis of the crystal pair (chord p in the figure) aligned with the RV outflow tract (62). Maximum and minimum principal deformation and angle of maximum principal deformation are then determined by solving for the eigenvalues of the deformation matrix determined from the product of the end-systolic crystal position matrix and the inverse of the end-diastolic crystal position matrix. The angle of the maximum principal deformation is then expressed relative to the long axis of the RV outflow tract and the assumed mean fiber direction as described (Meier et al., 1980). The principal deformations and angles are used as loading-condition dependent indices of regional contractility.

One tool for loading condition-independent assessment of regional RV contractility is the regional Frank-Starling relation. The regional Frank-Starling relation (sometimes referred to as the "preload-recruitable stroke work relation") has been extensively validated as a loading condition-independent index of contractility in both the LV (63) and the RV (64). It is reliable over large variations in LV pressure Chow, E, and DJ Farrar. Effects of left ventricular pressure reductions on right ventricular systolic performance and is superior to the end-systolic pressure dimension relation for in vivo assessment of LV and RV (65) contractile function under diverse conditions. The end-systolic pressure dimension relation has also been widely used as an index of global chamber contractility in isolated heart preparations. However, it tends to be nonlinear in vivo is less reliable than the Frank-Starling relation for assessment of global RV contractility, and is less reliable than the Frank-Starling relation for assessment of regional contractility after regional ischemia.

ELISA

The following is one example of an assay used to access the presence or absence of directed monoclonal antibody production. A selected antigen may be immobilized in PBS ($10^9$ particles or 5 μg/well) on High Binding Assay Plates (Costar eg. 24, 48 or 96-well plate). Control wells are coated with 2 mg bovine serum albumin (BSA) in PBS overnight at 4° C. Primary antibodies or control polyclonal species IgG (Sigma) are then incubated at a range of concentrations for 1 h at room temperature. The secondary antibody (anti-species-Fab alkaline phosphatase-conjugate, Sigma, 1:3000 in 3% BSA) is added and incubated for 1 h. The ELISA is developed with p-nitrophenyl phosphate (Sigma), and readings may be taken 1-4 h later at 405 nm (Reader 520, Organon Teknika).

All of the COMPOSITIONS, METHODS and APPARATUS disclosed and claimed herein can be made and executed without undue experimentation in light of the present disclosure. While the compositions and methods of this invention have been described in terms of preferred embodiments, it are apparent to those of skill in the art that variations maybe applied to the COMPOSITIONS, METHODS and APPARATUS and in the steps or in the sequence of steps of the methods described herein without departing from the concept, spirit and scope of the invention. More specifically, it are apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE 1

Metabolic measurements in RV myocardium of pigs undergoing one hour of acute RV pressure overload (all values are mean ± SEM).

| Measurement | Baseline | PAC (early) | PAC (late) | 1 hr post-PAC |
|---|---|---|---|---|
| Regional Myocardial Blood Flow (ml/gm-min) | 1.2 ± 0.1 | 2.1 ± 0.4 | 2.1 ± 0.3* | 2.0 ± 0.4 |
| Endocardial to Epicardial Blood Flow Ratio | 1.2 ± 0.1 | 1.2 ± 0.1 | 1.2 ± 0.1 | 1.3 ± 0.1 |
| Regional $MVO_2$ (mmol/kg-min) | 3.9 ± 0.5 | 7.1 ± 1.3 | 7.5 ± 1.7* | 5.5 ± 1.2 |
| Regional Lactate Consumption (mmol/kg-min) | 0.50 ± 0.08 | 0.63 ± 0.13 | 0.63 ± 0.19 | 0.53 ± 0.14 |
| Coronary Venous pH | 7.36 ± 0.02 | 7.36 ± 0.02 | 7.34 ± 0.02 | 7.32 ± 0.03 |

PAC: pressure overload from PA constriction.
*$p < .05$ vs. Baseline.

TABLE 2

Recovery of RV contractile function and alteration in desmin content of myocardium (as determined from 2D-PAGE gels) from pigs undergoing 90 min of acute RV pressure overload

| | Preload-adjusted regional external work (fraction of control, n = 4) | Desmin (fraction of total protein, n = 2) |
|---|---|---|
| Baseline | 1.00 | 0.019 |
| Recovery | 0.64 | 0.015 |

TABLE 3

Matrix metalloproteinase (MMP) assays from RV myocardium of pigs undergoing 90 min of acute RV pressure overload or 90 min sham pressure overload, in ng of enzyme/g wet weight tissue

| | Total Collagenase | | MMP-2 | | MMP-9 | |
|---|---|---|---|---|---|---|
| | Latent | Active | Latent | Active | Latent | Active |
| Sham | 51 ± 6 | N.D. | 294 ± 23 | 17 ± 2 | 54 ± 8 | 6 ± 1 |
| RVPO | 48 ± 7 | N.D. | 434 ± 30* | 24 ± 2* | 106 ± 17* | 8 ± 1 | significant differences ($p < .05$) are designated by *;
N.D. indicates Not Detectable.

TABLE 4

Proteins potentially related to RV dysfunction after acute pressure overload that will be quantified using ID-PAGE and Western blotting as part of Specific Objective #1. These proteins will also be identified on 2D-PAGE gels because their positive identification will permit more precise estimation of the molecular weights and pIs of unknown proteins of interest identified through the proteomics survey.

| Protein | pI Sequenced | MW (Da) in species | |
|---|---|---|---|
| Troponin-I | 9.87 | 23876 | human, mouse |
| "26 kDa" Troponin-I fragment ($TnI_{1-193}$) | 9.89 | 22098 | (theoretic, from human) |
| Troponin-T, cardiac isoform | 5.13 | 34459 | human, mouse |
| Tropomyosin α-chain | 4.69 | 32708 | pig |
| Myosin light chain kinase, skeletal muscle | 5.05 | 65685 | rat, rabbit |
| Myosin light chain 1, cardiac isoform | 5.03 | 21801 | human |
| Myosin light chain 2, cardiac isoform | 4.92 | 18658 | human, rat, mouse |
| Desmin | 5.21 | 53498 | pig |
| Vimentin, human | 5.06 | 53555 | human, mouse |
| Vimentin, pig, fragment | 6.47 | 30989 | pig |
| Protein kinase A, α-catalytic subunit | 5.75 | 18177 | pig, human, mouse |
| Protein kinase A, β-catalytic subunit | 8.84 | 40492 | human |

TABLE 4-continued

Proteins potentially related to RV dysfunction after acute pressure overload that will be quantified using ID-PAGE and Western blotting as part of Specific Objective #1. These proteins will also be identified on 2D-PAGE gels because their positive identification will permit more precise estimation of the molecular weights and pIs of unknown proteins of interest identified through the proteomics survey.

| Protein | pI Sequenced | MW (Da) in species | |
|---|---|---|---|
| Protein kinase A, β-catalytic subunit fragment | 8.68 | 39348 | pig |
| Protein kinase A, γ-catalytic subunit | 8.52 | 40281 | human |
| Actin, α-cardiac isoform | 5.23 | 42019 | pig |
| Calpain 1 (μ-calpain), catalytic subunit | 5.43 | 21944 | pig |
| Calpain 2 (m-calpain), catalytic subunit | 4.73 | 37808 | pig |
| Calpain, regulatory subunit | 5.05 | 28068 | pig |

TABLE 5

Proteins potentially related to RV dysfunction after acute pressure overload that will be quantified using 1D-PAGE and Western blotting as part of Specific Objective #1. These proteins will not be identified using 2D-PAGE because their size makes isoelectric focusing less consistent.

| Protein | MW (Da) | Sequenced in species |
|---|---|---|
| Calpastatin | 77124 | Pig |
| α-actinin 1, cytoskeletal form | 102974 | human |
| α-actinin 2, skeletal muscle form | 103854 | human |
| α-actinin 3, skeletal muscle isoform | 103294 | human |
| Spectrin, α-chain, brain | 284282 | human, mouse |
| Spectrin, β-chain, brain | 274631 | human, mouse |
| Integrin α-1 | 127838 | human |
| Integrin β-1 | 88465 | human |
| E-Cadherin | 97456 | human, mouse, cow |
| N-Cadherin | 99851 | human, mouse, cow |
| VE-Cadherin | 87546 | pig, human, mouse |
| Protein kinase C, multiple types | 76764 | human |
| Focal adhesion kinase | 119233 | human |
| Tensin | 187214 | chicken |

The invention claimed is:

1. A method comprising administering MDL-28170 to a subject diagnosed with right ventricular failure from right ventricular pressure overload (RVPO), wherein the administration of MDL-28170 attenuates the right ventricular failure.

2. The method of claim 1, wherein the RVPO is selected from the group consisting of one or more of massive pulmonary embolism, hypoxic pulmonary vasoconstriction, cardiopulmonary bypass and cardiac transplantation.

3. The method of claim 1, wherein the RVPO is acute.

4. The method of claim 1, wherein the RVPO is chronic.

* * * * *

UNITED STATES PATENT AND TRADEMARK OFFICE
CERTIFICATE OF CORRECTION

| | | |
|---|---|---|
| PATENT NO. | : 7,862,811 B2 | Page 1 of 1 |
| APPLICATION NO. | : 11/066839 | |
| DATED | : January 4, 2011 | |
| INVENTOR(S) | : Clifford Greyson et al. | |

It is certified that error appears in the above-identified patent and that said Letters Patent is hereby corrected as shown below:

In column 1, lines 6-8, delete
"The present invention was supported a National Heart, Lung and Blood Institute R01 grant HL68606." and insert
--This invention was made with government support under Grant HL-68606 awarded by the National Heart, Lung and Blood Institute, National Institutes of Health. The government has certain rights in the invention.-- therefor.

Signed and Sealed this
Twenty-first Day of June, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,862,811 B2 | Page 1 of 1 |
| APPLICATION NO. | : 11/066839 | |
| DATED | : January 4, 2011 | |
| INVENTOR(S) | : Greyson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1313 days.

Signed and Sealed this
Eleventh Day of October, 2011

David J. Kappos
*Director of the United States Patent and Trademark Office*